United States Patent
Doshi et al.

(10) Patent No.: US 7,856,979 B2
(45) Date of Patent: *Dec. 28, 2010

(54) NASAL RESPIRATORY DEVICES

(75) Inventors: Rajiv Doshi, Belmont, CA (US); Ryan Kendall Pierce, Carl Junction, MO (US); Bryan Loomas, Los Gatos, CA (US)

(73) Assignee: Ventus Medical, Inc., Belmont, CA (US)

( * ) Notice: Subject to any disclaimer, the term of this patent is extended or adjusted under 35 U.S.C. 154(b) by 217 days.

This patent is subject to a terminal disclaimer.

(21) Appl. No.: 11/805,496

(22) Filed: May 22, 2007

(65) Prior Publication Data

US 2007/0277832 A1    Dec. 6, 2007

Related U.S. Application Data

(60) Provisional application No. 60/808,034, filed on May 23, 2006.

(51) Int. Cl.
| | |
|---|---|
| A61G 10/00 | (2006.01) |
| A62B 7/00 | (2006.01) |
| A61M 15/08 | (2006.01) |
| A61M 16/00 | (2006.01) |
| A61F 5/56 | (2006.01) |
| A61B 19/00 | (2006.01) |
| A61B 19/08 | (2006.01) |

(52) U.S. Cl. ............... 128/206.11; 128/207.18; 128/204.18; 128/203.22; 128/200.26; 128/848; 128/849; 128/850; 128/851; 128/204.12; 128/204.13

(58) Field of Classification Search ............ 128/206.11, 128/207.18, 204.18, 203.22, 200.26, 848, 128/849, 850, 851, 204.12, 204.13; 137/512.1, 137/512.15

See application file for complete search history.

(56) References Cited

U.S. PATENT DOCUMENTS 628,111 A    7/1899    McHatton (Continued)

FOREIGN PATENT DOCUMENTS

EP    1157663 A1    11/2001

(Continued)

OTHER PUBLICATIONS

Sather et al.; U.S. Appl. No. 12/044,868 entitled "Respiratory sensor adapters for nasal devices," filed Mar. 7, 2008.

(Continued)

*Primary Examiner*—Patricia M Bianco
*Assistant Examiner*—Nihir Patel
(74) *Attorney, Agent, or Firm*—Shay Glenn LLP

(57) ABSTRACT

Described herein are nasal respiratory devices and methods for treating a variety of medical diseases including snoring and sleep apnea through the use of such devices. In general, these devices include an airflow resistor, such as a flap valve and a holdfast for securing the device in communication with the subject's nasal cavity. The devices may be configured to include leak paths to regulate the expiratory pressure when worn by a subject. Methods for using these devices may include securing a device over or at least partially within (or both of) a subject's nasal cavities.

26 Claims, 22 Drawing Sheets

U.S. PATENT DOCUMENTS

| | | |
|---|---|---|
| 669,098 A | 3/1901 | Overshiner |
| 675,275 A | 5/1901 | Gunning |
| 746,869 A | 12/1903 | Moulton |
| 774,446 A | 11/1904 | Moulton |
| 810,617 A | 1/1906 | Carence |
| 1,819,884 A | 8/1931 | Fores |
| 2,198,959 A | 4/1940 | Clarke |
| 2,237,954 A | 4/1941 | Wilson |
| 2,264,153 A | 11/1941 | Rowe |
| 2,274,886 A | 3/1942 | Carroll |
| 2,282,681 A | 5/1942 | Stotz |
| 2,335,936 A | 12/1943 | Hanlon |
| 2,433,565 A | 12/1947 | Korman |
| 2,448,724 A | 9/1948 | McGovney |
| 2,672,138 A | 3/1954 | Carlock |
| 2,751,906 A | 6/1956 | Irvine |
| 2,777,442 A | 1/1957 | Zelano |
| 3,145,711 A | 8/1964 | Beber |
| 3,370,305 A | 2/1968 | Goott et al. |
| 3,451,392 A | 6/1969 | Cook et al. |
| 3,463,149 A | 8/1969 | Albu |
| 3,513,839 A | 5/1970 | Vacante |
| 3,556,122 A * | 1/1971 | Laerdal .................. 137/102 |
| 3,695,265 A | 10/1972 | Brevik |
| 3,710,799 A | 1/1973 | Caballero |
| 3,722,509 A | 3/1973 | Nebel |
| 3,747,597 A | 7/1973 | Olivera |
| 3,884,223 A | 5/1975 | Keindl |
| 3,902,621 A | 9/1975 | Hidding |
| 4,004,584 A | 1/1977 | Geaney |
| 4,030,491 A | 6/1977 | Mattila |
| 4,040,428 A | 8/1977 | Clifford |
| 4,054,134 A | 10/1977 | Kritzer |
| 4,062,358 A | 12/1977 | Kritzer |
| 4,143,872 A | 3/1979 | Havstad et al. |
| 4,226,233 A | 10/1980 | Kritzer |
| 4,240,420 A | 12/1980 | Riaboy |
| 4,267,831 A | 5/1981 | Aguilar |
| 4,327,719 A | 5/1982 | Childers |
| RE31,040 E | 9/1982 | Possis |
| 4,354,489 A | 10/1982 | Riaboy |
| 4,403,616 A | 9/1983 | King |
| 4,456,016 A | 6/1984 | Nowacki et al. |
| 4,487,207 A | 12/1984 | Fitz |
| 4,533,137 A | 8/1985 | Sonne |
| 4,582,058 A | 4/1986 | Depel et al. |
| 4,601,465 A | 7/1986 | Roy |
| 4,640,277 A | 2/1987 | Meyer et al. |
| 4,739,987 A | 4/1988 | Nicholson |
| 4,822,354 A | 4/1989 | Elosegui |
| 4,854,574 A | 8/1989 | Larson et al. |
| 4,862,903 A | 9/1989 | Campbell |
| 4,908,028 A | 3/1990 | Colon et al. |
| 4,973,047 A | 11/1990 | Norell |
| 4,979,505 A | 12/1990 | Cox |
| 4,984,302 A | 1/1991 | Lincoln |
| 4,984,581 A | 1/1991 | Stice |
| 5,033,312 A | 7/1991 | Stupecky |
| 5,038,621 A | 8/1991 | Stupecky |
| 5,059,208 A | 10/1991 | Coe et al. |
| 5,078,739 A | 1/1992 | Martin |
| 5,092,781 A | 3/1992 | Casciotti et al. |
| 5,117,820 A | 6/1992 | Robitaille |
| 5,197,980 A | 3/1993 | Gorshkov et al. |
| 5,255,687 A | 10/1993 | McKenna |
| 5,383,470 A | 1/1995 | Kolbly |
| 5,385,542 A | 1/1995 | Rawlings |
| 5,391,205 A | 2/1995 | Knight |
| 5,392,773 A | 2/1995 | Bertrand |
| 5,394,867 A | 3/1995 | Swann |
| 5,415,660 A | 5/1995 | Campbell et al. |
| 5,425,359 A | 6/1995 | Liou |
| 5,459,544 A | 10/1995 | Emura |
| 5,522,382 A | 6/1996 | Sullivan et al. |
| 5,562,641 A | 10/1996 | Flomenblit et al. |
| 5,568,808 A | 10/1996 | Rimkus |
| 5,607,469 A | 3/1997 | Frey |
| 5,649,533 A | 7/1997 | Oren |
| 5,665,104 A | 9/1997 | Lee |
| 5,740,798 A | 4/1998 | McKinney |
| 5,743,256 A | 4/1998 | Jalowayski |
| 5,763,979 A | 6/1998 | Mukherjee et al. |
| 5,775,335 A | 7/1998 | Seal |
| 5,782,896 A | 7/1998 | Chen et al. |
| 5,797,920 A | 8/1998 | Kim |
| 5,823,187 A | 10/1998 | Estes et al. |
| 5,865,170 A | 2/1999 | Moles |
| 5,876,434 A | 3/1999 | Flomenblit et al. |
| 5,890,998 A | 4/1999 | Hougen |
| 5,899,832 A | 5/1999 | Hougen |
| 5,910,071 A | 6/1999 | Hougen |
| 5,911,756 A | 6/1999 | Debry |
| 5,947,119 A | 9/1999 | Reznick |
| 5,954,766 A | 9/1999 | Zadno-Azizi et al. |
| 5,957,978 A | 9/1999 | Blom |
| 5,992,006 A | 11/1999 | Datsikas |
| 6,004,342 A | 12/1999 | Filis |
| 6,083,141 A | 7/2000 | Hougen |
| D430,667 S | 9/2000 | Rome |
| 6,119,690 A | 9/2000 | Pantaleo |
| 6,165,133 A | 12/2000 | Rapoport et al. |
| 6,177,482 B1 | 1/2001 | Cinelli et al. |
| 6,258,100 B1 | 7/2001 | Alferness et al. |
| 6,287,290 B1 | 9/2001 | Perkins et al. |
| 6,293,951 B1 | 9/2001 | Alferness et al. |
| 6,369,126 B1 | 4/2002 | Cinelli et al. |
| 6,398,775 B1 | 6/2002 | Perkins et al. |
| 6,439,233 B1 | 8/2002 | Geertsema |
| 6,484,725 B1 | 11/2002 | Chi |
| 6,500,095 B1 | 12/2002 | Hougen |
| 6,510,846 B1 | 1/2003 | O'Rourke |
| 6,527,761 B1 | 3/2003 | Soltesz et al. |
| 6,561,188 B1 * | 5/2003 | Ellis .................. 128/206.11 |
| 6,562,057 B2 | 5/2003 | Santin |
| 6,568,387 B2 | 5/2003 | Davenport et al. |
| 6,581,598 B1 | 6/2003 | Foran et al. |
| 6,585,639 B1 | 7/2003 | Kotmel et al. |
| 6,592,594 B2 | 7/2003 | Rimbaugh et al. |
| 6,592,995 B2 | 7/2003 | Topolkaraev et al. |
| 6,595,215 B2 | 7/2003 | Wood |
| 6,626,172 B1 | 9/2003 | Karow et al. |
| 6,626,179 B1 * | 9/2003 | Pedley .................. 128/857 |
| 6,631,721 B1 | 10/2003 | Salter et al. |
| 6,679,264 B1 | 1/2004 | Deem et al. |
| 6,694,979 B2 | 2/2004 | Deem et al. |
| 6,722,360 B2 | 4/2004 | Doshi |
| 6,726,598 B1 | 4/2004 | Jarvis et al. |
| 6,737,160 B1 | 5/2004 | Full et al. |
| 6,769,432 B1 | 8/2004 | Keifer |
| 6,776,162 B2 | 8/2004 | Wood |
| 6,848,446 B2 | 2/2005 | Noble |
| 6,863,066 B2 | 3/2005 | Ogle |
| 6,872,439 B2 | 3/2005 | Fearing et al. |
| 6,921,574 B2 | 7/2005 | Cinelli et al. |
| 6,997,177 B2 | 2/2006 | Wood |
| 7,011,723 B2 | 3/2006 | Full et al. |
| 7,047,969 B2 | 5/2006 | Noble |
| 7,156,098 B2 | 1/2007 | Dolezal et al. |
| 7,175,723 B2 | 2/2007 | Jones et al. |
| 7,178,524 B2 | 2/2007 | Noble |
| 7,201,169 B2 | 4/2007 | Wilkie et al. |
| D542,407 S | 5/2007 | Stallard et al. |
| 7,263,996 B2 | 9/2007 | Ho |
| 2001/0051799 A1 | 12/2001 | Ingenito |

| | | | |
|---|---|---|---|
| 2001/0056274 A1 | 12/2001 | Perkins et al. | |
| 2002/0062120 A1 | 5/2002 | Perkins et al. | |
| 2002/0077593 A1 | 6/2002 | Perkins et al. | |
| 2002/0112729 A1 | 8/2002 | DeVore et al. | |
| 2003/0024527 A1 | 2/2003 | Ginn | |
| 2003/0050648 A1 | 3/2003 | Alferness et al. | |
| 2003/0070682 A1 | 4/2003 | Wilson et al. | |
| 2003/0106555 A1 | 6/2003 | Tovey | |
| 2003/0106556 A1 | 6/2003 | Alperovich et al. | |
| 2003/0140925 A1 | 7/2003 | Sapienza et al. | |
| 2003/0154988 A1 | 8/2003 | DeVore et al. | |
| 2003/0158515 A1 | 8/2003 | Gonzalez et al. | |
| 2003/0195552 A1 | 10/2003 | Santin | |
| 2003/0209247 A1 | 11/2003 | O'Rourke | |
| 2004/0016432 A1 | 1/2004 | Genger et al. | |
| 2004/0020492 A1 | 2/2004 | Dubrul et al. | |
| 2004/0020493 A1 | 2/2004 | Wood | |
| 2004/0055606 A1 | 3/2004 | Hendricksen et al. | |
| 2004/0112379 A1 | 6/2004 | Djupesland | |
| 2004/0194779 A1 | 10/2004 | Doshi | |
| 2004/0254491 A1 | 12/2004 | Ricciardelli | |
| 2004/0261791 A1 | 12/2004 | Horian | |
| 2004/0261798 A1 | 12/2004 | Rimkus | |
| 2005/0011524 A1 | 1/2005 | Thomlinson et al. | |
| 2005/0033344 A1 | 2/2005 | Dillard et al. | |
| 2005/0051170 A1 | 3/2005 | Koo | |
| 2005/0284479 A1 | 12/2005 | Schrader et al. | |
| 2006/0085027 A1 | 4/2006 | Santin et al. | |
| 2006/0144398 A1 | 7/2006 | Doshi et al. | |
| 2006/0150978 A1 | 7/2006 | Doshi et al. | |
| 2006/0150979 A1 | 7/2006 | Doshi et al. | |
| 2006/0283461 A1 | 12/2006 | Lubke et al. | |
| 2007/0051364 A1 | 3/2007 | Jacobson et al. | |
| 2007/0095349 A1 | 5/2007 | Hansmann et al. | |
| 2007/0175478 A1 | 8/2007 | Brunst | |
| 2007/0227542 A1* | 10/2007 | Kashmakov et al. | 128/206.11 |
| 2007/0283962 A1 | 12/2007 | Doshi et al. | |
| 2007/0295338 A1* | 12/2007 | Loomas et al. | 128/207.18 |
| 2008/0221470 A1* | 9/2008 | Sather et al. | 600/533 |
| 2009/0145441 A1 | 6/2009 | Doshi et al. | |
| 2009/0145788 A1 | 6/2009 | Doshi et al. | |
| 2009/0188493 A1 | 7/2009 | Doshi et al. | |
| 2009/0194100 A1 | 8/2009 | Minagi | |
| 2009/0194109 A1 | 8/2009 | Doshi et al. | |

FOREIGN PATENT DOCUMENTS

| | | |
|---|---|---|
| EP | 1205203 A2 | 5/2002 |
| GB | 2324729 A | 4/1998 |
| RU | 2048820 C1 | 11/1995 |
| SU | 1586709 A1 | 8/1990 |
| WO | WO 90/12614 A1 | 11/1990 |
| WO | WO 95/17220 A1 | 6/1995 |
| WO | WO 95/33520 A1 | 12/1995 |
| WO | WO 99/03395 A1 | 1/1999 |
| WO | WO 00/29066 A1 | 5/2000 |
| WO | WO 00/50121 A1 | 8/2000 |
| WO | WO 00/67848 A1 | 11/2000 |
| WO | WO 01/02042 A1 | 1/2001 |
| WO | WO 01/13839 A1 | 3/2001 |
| WO | WO 01/13908 A2 | 3/2001 |
| WO | WO 01/49371 A2 | 7/2001 |
| WO | WO 01/87170 A1 | 11/2001 |
| WO | WO 01/89381 A1 | 11/2001 |
| WO | WO 02/38038 A2 | 5/2002 |
| WO | WO 03/022124 A2 | 3/2003 |
| WO | WO 03/034927 A1 | 5/2003 |
| WO | WO 2004/084998 A1 | 10/2004 |
| WO | WO 2006/063339 A2 | 6/2006 |
| WO | WO 2007/129814 A1 | 11/2007 |
| WO | WO 2007/134458 A1 | 11/2007 |

OTHER PUBLICATIONS

Pierce et al.; U.S. Appl. No. 12/141,875 entitled "Adhesive nasal respiratory devices," filed Jun. 18, 2008.

Sather et al.; U.S. Appl. No. 12/405,837 entitled "Nasal devices with noise-reduction and methods of use," filed Mar. 17, 2009.

Ferdinand et al.; U.S. Appl. No. 12/485,750 entitled "Adjustable resistance nasal devices," filed Jun. 16, 2009.

Hakel et al.; Nasal obturator for velopharyngeal dysfunction in dysarthria: technical report on a one-way valve; Journal of Medical Speech-Language Pathology; vol. 12; No. 4; pp. 155-159; 2004.

Doshi et al.; U.S. Appl. No. 12/711,782 entitled "Respiratory devices," filed Feb. 24, 2010.

Doshi et al; U.S. Appl. No. 11/811,339 entitled "Nasal devices," filed Jun. 7, 2007.

Doshi et al; U.S. Appl. No. 11/941,913 entitled "Nasal device applicators," filed Nov. 16, 2007.

Doshi et al; U.S. Appl. No. 11/941,915 entitled "Adjustable nasal devices," filed Nov. 16, 2007.

Doshi, Rajiv; U.S. Appl. No. 12/014,060 entitled "Methods and devices for improving breathing in patients with pulmonary disease," filed Jan. 14, 2008.

Mahadevia, A. K. et al., Effects of expiratory positive airway pressure on sleep-induced respiratory abnormalities in patients with hypersomnia-sleep apnea syndrome, Am Rev Respir Dis 1983, vol. 128, pp. 708-711, Oct. 1983.

Dillard, D. et al., Evaluation of a novel intra-bronchial valve to produce lung volume reduction, World Congress of Bronchology, Jun. 2002 (figs. 1-4 available upon request).

http://chinookmed.com/index.cfm/fa/product.display&Product_ID=275.

* cited by examiner

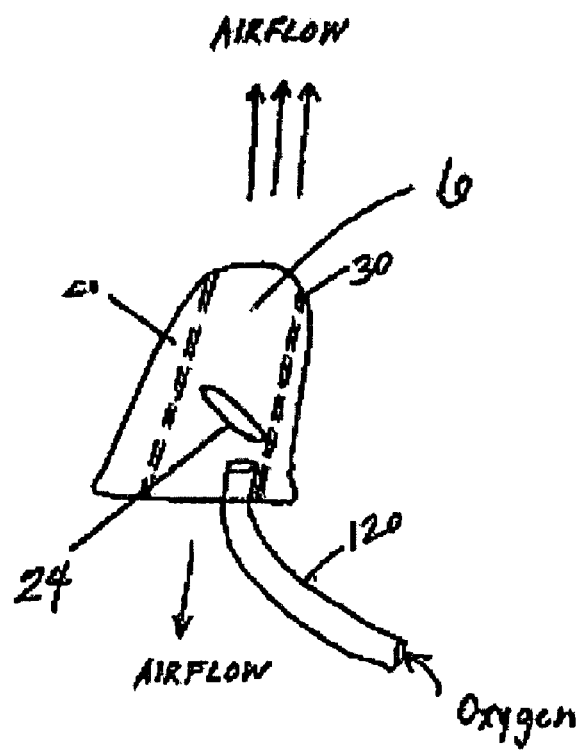
FIG. 24
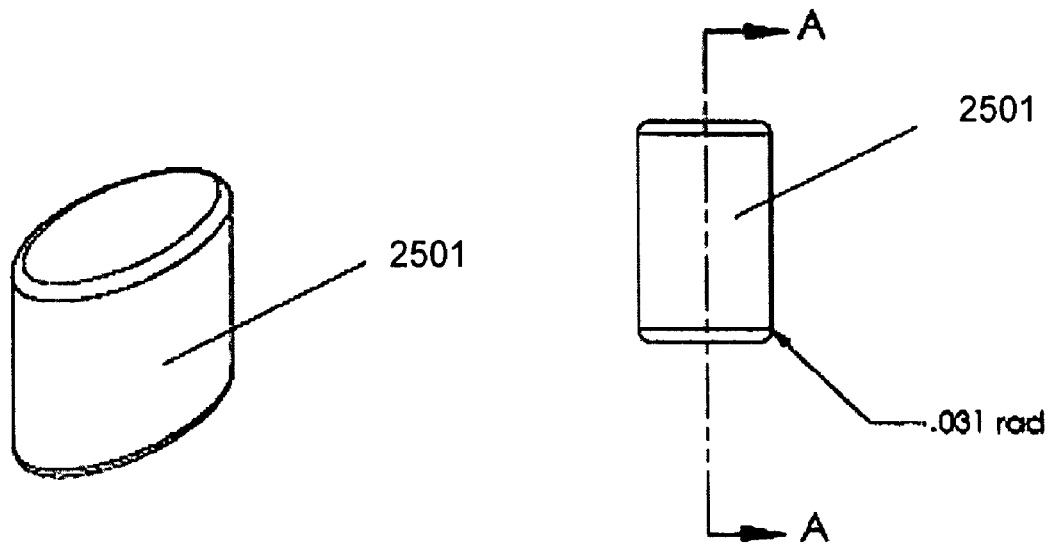
FIG. 25
FIG. 26

NASAL RESPIRATORY DEVICES

CROSS-REFERENCE TO RELATED APPLICATIONS

This application claims priority to U.S. Provisional Patent Application 60/808,034, filed May 23, 2006.

BACKGROUND

Numerous disease states could benefit from the modification of subject respiration, including heart failure, sleep disordered breathing (e.g., sleep apnea, etc.) and other sleep disorders (e.g., snoring), hypertension, chronic obstructive pulmonary disease (COPD), bronchitis, asthma, and many others.

Heart failure, or congestive heart failure (CHF), is a common clinical syndrome that represents the end-stage of a number of pulmonary and cardiac disease states. Heart failure is a degenerative condition that occurs when the heart muscle weakens and the ventricle no longer contracts normally. The heart can then no longer adequately pump blood to the body including the lungs. This may lead to exercise intolerance, or may cause fluid retention with subsequent shortness of breath or swelling of the feet. Over four million people are diagnosed with heart failure in the United States alone. Morbidity and mortality in subjects with heart failure is high.

Sleep apnea is one form of sleep disordered breathing. Sleep apnea is defined as the temporary absence or cessation of breathing during sleep. Airflow must be absent for some period of time longer than the usual inter-breath interval, typically defined as ten seconds for adults and eight seconds (or more than two times the normal respiratory cycle time) for infants. There are several general varieties of sleep apnea: central, obstructive, complex, and mixed. In central sleep apnea, the subject makes no effort to breathe. In obstructive apnea, ventilatory effort is present, but no airflow results, because of upper airway closure. In mixed apnea, there is initially no ventilatory effort (suggestive of central sleep apnea), but an obstructive sleep apnea pattern becomes evident when ventilatory effort resumes. Finally, hypopnea is a temporary decrease in inspiratory airflow relative to the previous several inspirations. The terms sleep apnea and/or sleep disordered breathing may refer to hypopnea.

Hypertension refers to elevated blood pressure, and is a very common disease. Hypertension is characterized by elevated systolic and/or diastolic blood pressures. Despite the prevalence of hypertension and its associated complications, control of the disease is far from adequate. Only a third of people with hypertension control their blood pressure adequately. This failure reflects the inherent problem of maintaining long-term therapy for a usually asymptomatic condition, particularly when the therapy may interfere with the subject's quality of life, and when the immediate benefits of the therapy are not obvious to the subject.

Chronic obstructive pulmonary disease (COPD) includes chronic bronchitis, emphysema and asthma. In both chronic bronchitis and emphysema, airflow obstruction limits the subject's airflow during exhalation. COPD is a progressive disease characterized by a worsening baseline respiratory status over a period of many years with sporadic exacerbations often requiring hospitalization. Early symptoms include increased sputum production and sporadic acute exacerbations characterized by increased cough, purulent sputum, wheezing, dyspnea, and fever. As the disease progresses, the acute exacerbations become more frequent. Late in the course of the disease, the subject may develop hypercapnia, hypoxemia, erythrocytosis, cor pulmonale with right-sided heart failure, and edema.

Chronic bronchitis is characterized by a chronic cough with sputum production leading to obstructed expiration. Pathologically, there may be mucosal and submucosal edema and inflammation and an increase in the number and size of mucus glands. Emphysema is characterized by destruction of the lung parenchyma leading to loss of elastic recoil, reduced tethering of airways, and obstruction to expiration. Pathologically, the distal airspaces are enlarged.

Asthma is another chronic lung condition, characterized by difficulty in breathing. People with asthma have extra-sensitive or hyper-responsive airways. The airways react by obstructing or narrowing when they become inflamed or irritated. This makes it difficult for the air to move in and out of the airways, leading to respiratory distress. This narrowing or obstruction can lead to coughing, wheezing, shortness of breath, and/or chest tightness. In some cases, asthma may be life threatening.

In all of these diseases, current medical and surgical therapies are not completely effective, and there is considerable room for improvement. Two therapies that are used to treat these diseases are pulmonary rehabilitation (including pursed-lip breathing) and non-invasive mechanical ventilation.

Pulmonary rehabilitation is frequently used to treat subjects suffering from a variety of medical ailments such as those mentioned. For example, COPD subjects are taught new breathing techniques that reduce hyperinflation of the lungs and relieve expiratory airflow obstruction. One of the goals of this training is to reduce the level of dyspnea. Typically, these new breathing techniques include diaphragmatic and pursed-lip breathing. Pursed-lip breathing involves inhaling slowly through the nose and exhaling through pursed-lips (as if one were whistling), taking two or three times as long to exhale as to inhale. Most COPD subjects instinctively learn how to perform pursed-lip breathing in order to relieve their dyspnea. Moreover, subjects with asthma and other respiratory ailments, and even normal people during exercise, have been shown to use pursed-lip breathing, especially during times of exertion.

It is widely believed that producing a proximal obstruction (e.g., pursing the lips) splints open the distal airways that have lost their tethering in certain disease states. In other words, airways that would normally collapse during respiration remain open when the subject breathes through pursed-lips. Moreover, by increasing exhalation time, respiratory rate can be reduced and, in some cases, made more regular.

The medical literature has confirmed the utility of pursed-lip breathing in COPD subjects. Specifically, it has been found that pursed-lip breathing by COPD subjects results in a reduction in respiratory rate, an increase in tidal volumes, and an improvement of oxygen saturation. All of these effects contribute to a reduction in subject dyspnea. However, pursed-lip breathing requires conscious effort. Thus, the subject cannot breathe through pursed-lips while sleeping. As a result, the subject can still become hypoxic at night and may develop pulmonary hypertension and other sequelae as a result. Furthermore, the subject has to constantly regulate his own breathing. This interferes with his performing of other activities because the subject must pay attention to maintaining pursed-lip breathing.

Non-invasive positive pressure ventilation (NPPV) is another method of treating diseases that benefit from regulation of the subject's respiration. NPPV refers to ventilation delivered by a nasal mask, nasal prongs/pillows or face mask. NPPV eliminates the need for intubation or tracheostomy.

Outpatient methods of delivering NPPV include bilevel positive airway pressure (BIPAP or bilevel) ventilator devices, or continuous positive airway pressure (CPAP) devices.

NPPV can deliver a set pressure during each respiratory cycle, with the possibility of additional inspiratory pressure support in the case of bi-level devices. NPPV has been shown to be very efficacious in such diseases as sleep apnea, heart failure, and COPD, and has become increasingly used in recent years. Many subjects use CPAP or BIPAP at night while they are sleeping.

However, most subjects experience difficulty adapting to nocturnal NPPV, leading to poor compliance. Mask discomfort is a very common problem for subjects new to NPPV, because of the high pressures on the nose, mouth, and face, and because of uncomfortably tight straps. Nasal congestion and dryness are also common complaints that may vary by season. The nasal bridge can become red or ulcerated due to excessive mask tension. Eye irritation and acne can also result. Still other subjects experience abdominal distention and flatulence. Finally, air leakage through the mouth is also very common in nasal NPPV subjects, potentially leading to sleep arousals.

Both pursed-lip breathing and the use of NPPV have been shown to offer significant clinical benefits to subjects with a variety of medical illnesses, including but not limited to COPD, heart failure, pulmonary edema, sleep apnea (both central and obstructive) and other sleep disordered breathing, cystic fibrosis, asthma, cardiac valve disease, arrhythmias, anxiety, and snoring. Expiratory resistance is believed to provide the bulk of clinical improvements when using pursed-lip breathing and NPPV, through a variety of physiologic mechanisms. In contrast, inspiratory support is not believed to offer clinical benefits in many subjects. For example, in COPD, expiratory resistance facilitates expiration, increases tidal volume, decreases respiratory rate, and improves gas exchange. In the case of heart failure, it is felt that positive pressure in the airways (due to expiratory resistance) reduces pulmonary edema and improves lung compliance, decreases preload and afterload, increases $pO_2$, and decreases $pCO_2$. In many disease states, expiratory resistance helps maintain a more stable respiratory rate that can have profound clinical effects to the subject.

It would therefore be desirable to have a medical device and/or procedure that mimics the effect of pursed-lip breathing and/or the benefits of non-invasive ventilation without suffering from the drawbacks described above.

General respiratory devices addressing many of these problems may be found in U.S. patent application Ser. No. 11/298,640, filed Dec. 8, 2005, herein incorporated by reference in its entirety. Described herein are respiratory devices and methods of using them that include many features not previously developed or described.

BRIEF SUMMARY

Described herein are nasal respiratory devices and methods for treating a variety of medical diseases through the use of such devices. In general, these devices include a rim configured as a substantially tubular body enclosing a passageway, an airflow resistor within the passageway (where the airflow resistor is typically a flap valve), and a holdfast for securing the respiratory device within a nasal cavity.

The respiratory devices described herein may include a passageway, a flap valve in communication with the passageway, a flap valve support located adjacent to the flap valve (wherein the flap valve support is configured to prevent the flap valve from opening in more than one direction), and a holdfast. The holdfast is configured to secure the passageway of the device respiratory device in communication with the nasal cavity without covering the subject's mouth. Any of the devices described herein may be removably secured in communication with a nasal cavity (e.g., over and/or at least partially within the subject's nasal cavity). Thus, the nasal devices described herein typically interact with the subject's nose but do not cover the subject's mouth.

The nasal devices described herein may also include at least one leak path. As described in greater detail below, a leak path allows air to flow through or past the respiratory device even when the airflow resistor is closed. In some variations, the devices includes one or more leak paths through the device that are not formed though a flap of the flap valve (for example, a leak path may be formed through a body or holdfast portions of the device).

In some variations, the device includes a flap valve that is a continuously flexible flap valve. A continuously flexible flap valve is flexible along the majority (or entirety) of the flap. For example, the flap of the flap valve may be made of silicone. Furthermore, the flap of the flap valve may have a thickness that is sufficient to allow the flap to bend or flex along the movable length of the flap.

The devices may be secured over, across, and/or within a subject's nose. For example, the holdfast may be configured to secure the respiratory device over the subject's nasal cavity. In some variations, the holdfast is configured to secure the respiratory device at least partially within the subject's nasal cavity. In some variations, the holdfast is configured to secure the respiratory device in communication with one of the subject's nostrils, or both of the subject's nostrils. A holdfast may be made of a foam (or foamed) material. For example, the holdfast may be made of foamed polyurethane.

Further, the devices described herein may also include a substantially tubular body forming the passageway. The substantially tubular body may have an elliptical cross-section. Thus, the devices may include a rim (or rim body) forming the tubular body.

A nasal respiratory device may also include a valve seal surface within the passageway configured to seat the edge of the flap valve when the flap valve is closed. The valve seal surface may be, for example a lip protruding into the circumference of the passageway.

A flap valve support may be a mesh, crossbeam, pin, or the like, that can abut the flap of a flap valve to prevent it from bending in an undesirable direction (e.g., preventing the valve from opening in any direction but the appropriate direction). For example, a flap valve support may include at least one crossbeam spanning the passageway. In some variations, the flap valve support includes a pair of intersecting crossbeams.

Some variations of the devices described herein include a flap valve aligner that is configured to keep a flap (or flaps) of the flap valve oriented within the opening of a passage through the device. For example, a flap valve aligner may be a post or posts projecting from a crossbeam spanning the passageway, wherein the flap valve aligner orients the flap valve within the passageway by securing the hinge (or central region) of the flap on the post(s). In this example, the post(s) may pass through an opening (or openings) on the flap of the flap valve.

Also described herein are nasal respiratory devices configured to be secured in communication with a subject's nasal cavity that include an airflow resistor configured to inhibit expiration more than inspiration and a holdfast configured to secure the device in communication with the subject's nasal cavity without covering the subject's mouth, wherein device has a resistance to expiration that is between about 0.001 and about 0.25 cm $H_2O$/ml/sec, and a resistance to inhalation that is between about 0.0001 and about 0.05 cm $H_2O$/ml/sec, when resistance is measured at 100 ml/sec. In some variations the nasal respiratory device has a resistance to expiration that is between about 0.03 cm $H_2O$/ml/sec and about 0.2 cm $H_2O$/ml/sec, or between about 0.03 and about 0.15 cm $H_2O$/ml/sec. In some variations, the nasal respiratory device has a resistance to inhalation that is between about 0.001 and about 0.02 cm $H_2O$/ml/sec, or between about 0.001 and about 0.01 cm $H_2O$/ml/sec. In some variations, the devices include one or more leak paths. The resistance to inspiration and the resistance to expiration may be determined by the airflow resistor and the total leak path.

Any of these nasal respiration devices may include an airflow resistor that is a flap valve, as described above. Further, the devices may include at least one leak path that is not formed though a movable portion of the airflow resistor (e.g., a flap of a flap valve).

Any of the holdfasts or configurations of holdfasts described above may be used as well. For example, the nasal respiratory device may include a holdfast configured to secure the device in communication with the subject's nasal cavity.

Also described herein are nasal respiratory device including a passageway having an opening, a flap valve in communication with the opening, a flap valve aligner aligning a flap of the flap valve in communication with the opening, and a holdfast configured to secure the respiratory device in communication with a subject's nasal cavity. As described above, these nasal respiratory devices may include one or more leak paths, include leak paths that are not formed though the flap of the flap valve. The flap valve may have a continuously flexible flap.

The nasal respiratory devices may be secured over, at least partially over, across, and/or at least partially within a subject's nose (e.g., via the holdfast). The holdfast may be configured to secure the respiratory device in communication with one of the subject's nostrils, or both of the subject's nostrils. In some variations, the nasal respiratory device also includes a flap valve support. The nasal respiratory devices described herein are typically secured over, at least partially over, across, or at least partially within a subject's nose, but not over (e.g., covering) the subject's mouth. Thus, in many variations, these devices are in communication with the subject's nose (e.g., over or at least partially within the subject's nose) without covering or obscuring the subject's mouth and the subject may breathe through the mouth even while breathing through the nose is regulated.

Also described herein are methods of treating a disorder including the steps of allowing the subject to breathe through the mouth without additional resistance while inhibiting nasal expiration more than nasal inhalation, and inhibiting nasal expiration more than nasal inspiration by providing a resistance to nasal expiration that is between about 0.04 and about 0.5 cm $H_2O$/ml/sec, and a resistance to nasal inhalation that is between about 0.0002 and about 0.1 cm $H_2O$/ml/sec measured at a flow rate of 50 ml/sec. The method may also include the steps of securing a respiratory device in communication with the subject's nasal cavity, wherein the respiratory device comprises an airflow resistor that inhibits expiration more then inhalation. The disorder treated may be selected from the group consisting of: sleep disordered breathing or snoring.

Also described herein are methods of treating a disorder comprising the steps of a nasal respiratory device in communication with a subject's nasal cavity, wherein the respiratory device comprises a flap valve and a flap valve support adjacent to the flap valve, and the flap valve support is configured to prevent the flap valve from opening in more than one direction. The disorder treated is selected from the group consisting of: sleep disordered breathing or snoring.

Also described herein are methods of treating a disorder including the steps of securing a nasal respiratory device in communication with a subject's nasal cavity, wherein the respiratory devices comprises a flap valve and a flap valve aligner aligning a flap of the flap valve in communication with an opening through the nasal respiratory device. The disorder treated is selected from the group consisting of: sleep disordered breathing or snoring.

General respiratory devices addressing many of these problems may be found in U.S. patent application Ser. No. 11/298,640, filed Dec. 8, 2005, herein incorporated by reference in its entirety. Described herein are respiratory devices and methods of using them that include many features not previously developed or described.

INCORPORATION BY REFERENCE

All publications and patent applications mentioned in this specification are herein incorporated by reference in their entirety to the same extent as if each individual publication or application was specifically and individually indicated to be incorporated by reference.

BRIEF DESCRIPTION OF THE DRAWINGS

FIG. 7a shows the device during inhalation, and FIG. 7b shows the device during exhalation.

FIG. 15a shows the airflow resistor during higher levels of exhalation airflow and/or FIG. 15b shows the airflow resistor during lower levels of exhalation airflow and/or FIG. 15c shows the airflow resistor during inhalation.

FIG. 24 shows a cross-sectional view of another respiratory device where the device is removable and adapted for the nasal cavity.

FIG. 25 shows a perspective view of the rim portion of one example of a respiratory device as described herein.

FIGS. 26, 27, and 28 show side, top, and cross-sectional views of the rim portion shown in FIG. 25.

DETAILED DESCRIPTION

Figure 1:
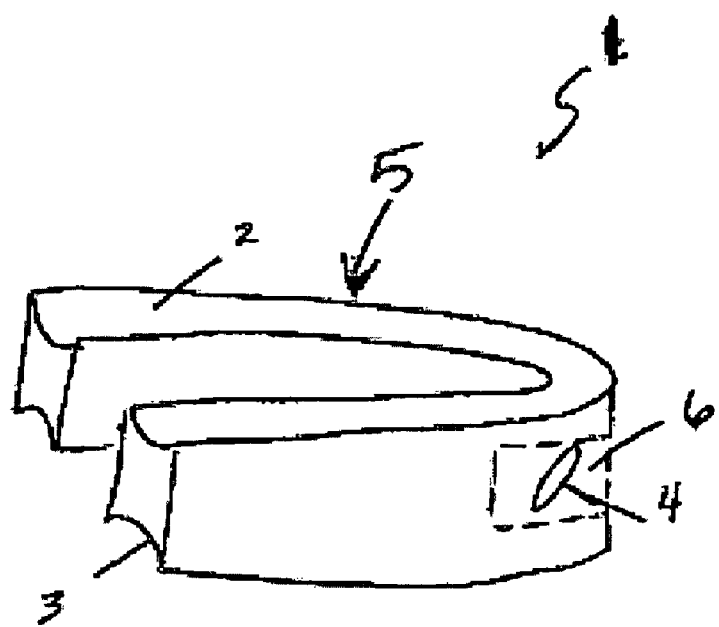
FIG. 1 is a perspective view of a respiratory device adapted for an oral cavity.

Respiratory devices, kits, and methods for their use in improving respiratory and cardiovascular function are described herein. In general, these respiratory devices are referred to as respiratory devices or simply as "devices." The devices and methods described herein may be useful to treat a variety of medical disease states, and may also be useful for non-therapeutic purposes. The devices and methods described herein are not limited to the particular embodiments described. Variations of the particular embodiments may be made and still fall within the scope of the appended claims. It is also to be understood that the examples and particular embodiments described are not intended to be limiting. Instead, the scope of the present invention will be established by the appended claims.

As used in this specification, the singular forms "a," "an," and "the" include plural reference unless the context clearly dictates otherwise. Unless defined otherwise, all technical and scientific terms used herein have the same meaning as commonly understood by one of ordinary skill in the art.

Devices

The respiratory devices described herein alter airflow into and out of the lungs through a respiratory cavity such as the mouth and/or the nostrils of the nose. The respiratory devices typically include an airflow resistor capable of at least partially obstructing airflow, particularly airflow in one direction (e.g., expiration) more than the opposite direction (e.g., inhalation). In particular, the respiratory devices include an airflow resistor exemplified by a flap valve. Additional examples of airflow resistors are also described herein. These respiratory devices may be used to increase the resistance to expiration during the expiratory phase of the respiratory cycle. Many of the respiratory devices described herein may prevent collapse of airways and airflow conduits. Flap valves are described in greater detail below.

The respiratory devices described herein generally include an airflow passageway and an airflow resistor. The airflow passageway (or "passageway") generally defines a channel allowing the passage of air. The passageway may be of any suitable size or shape; however it is configured so that when the respiratory device is worn by a subject, the passageway provides an opening leading toward the subject's lungs in fluid connection with an opening that leads away from the subject's lungs. The terms "patient" and "subject" are used to describe any user of the respiratory device, including users who are not using the respiratory device for therapeutic purposes. The airflow passageway may be any suitable length. For example, the passageway may be as short as the airflow resistor will allow (e.g., substantially just an opening that is regulated by the airflow resistor). Similarly, the airflow passageway may be longer than the space required to support the airflow resistor. For example, in versions of the respiratory device adapted for at least partial insertion into a nasal cavity, the airflow passageway may be approximately as long as the length of an average nares. In some versions, the passageway extends the length of an average nasal chamber.

The neutral cross-sectional area of the passageway may be of any appropriate size. Neutral cross-sectional area may refer to the cross-sectional area of the passageway when the device allows air to flow through the passageway without additional resistance (e.g., due to an airflow resistor). In particular, the size (e.g., diameter) or shape of the passageway may depend upon configuration of the respiratory device. For example, respiratory devices configured to be inserted within the nasal cavity (e.g., a nasal chamber) may have an area that is approximately the area of a narrow portion of the nasal cavity, or slightly narrower. Respiratory devices configured to be secured over an oral cavity or a nasal cavity may have passageways of larger diameters. Furthermore, the cross-sectional area of a passageway may vary along the length of the device.

The airflow passageway may comprise a dedicated structure defining the inner wall of the airflow passageway, or it may be a structural component of the device. For example, the passageway may comprise a passage wall defined by a rim. A rim may be a tube (or tunnel) of material of any appropriate thickness. The rim may also be a frame, rather than a complete tube. The rim may comprise a sufficiently rigid material so that it can support the passageway, and prevent the passageway from collapsing during use and during respiration. In some versions, at least a portion of the rim is made of a compressible material that may be compressed to facilitate insertion and removal, while maintaining the ability to support the passageway and prevent complete collapse of the passageway during respiration. The rim may also be somewhat compressible during respiratory flow, or alternatively, it may be rigid. The airflow passageway (including a rim portion) may also serve as an attachment site for other components such as airflow resistors, filters, anchors, holdfast etc.

A rim may be any suitable shape or size. For example, a rim may comprise a ring shape or an oval shape. As mentioned above, a rim may define the inner diameter of the passageway. In some versions, the rim comprises a material having strength sufficient to prevent the collapse of a respiratory device that has been inserted into a nasal cavity. For example, the rim may comprise a metal, a polymer (particularly stiff polymers), etc. In some versions, the rim may comprise softer or "weaker" materials which are formed or arranged so that the final shape of the rim has sufficient strength to prevent the collapse of the respiratory device during use.

As mentioned above, a respiratory device may include a rim that is a tube or tubular body having a distal end and a proximal end, through which the airflow passageway extends. In variations of the device that are adapted to be secured in a subject's nasal cavity, the distal end of the respiratory device is inserted first into the subject's nose, so that the device is worn so that during inhalation air flows from the proximal to the distal end of the passageway, and during expiration air flows from the distal to proximal end of the passageway. In some variations, the proximal end of the tubular body has different properties from the distal end. For example, the thickness of the tubular body from distal end to proximal end may vary.

In some variations, the respiratory device has a tubular body in which the distal end is more compliant than the proximal end. Thus, the distal end may be more readily compressed for insertion into the nasal cavity, while the proximal end is somewhat more rigid, allowing for easier removal/insertion of the device. A more compliant distal end may also help the device better fit a subject wearing the device, and may enhance comfort. As described more fully below, the distal region of the device may conform to fit the nasal cavity.

In some variations, the distal end is more compliant than the proximal end because different regions of the tubular body are made from different materials or have different structures. For example, a distal portion of the tubular body may have a wall thickness that is less than the wall thickness of the more proximal portion of the tubular body, as described in more detail below when discussing FIGS. 25-28. The rim (e.g., tubular body) may have two or more regions of different wall thickness, or it may have regions of continuously varying thickness. The wall thickness may be uniform for a given distal-to-proximal position (e.g., along the length of a respiratory device's tubular body). As mentioned above, the wall thickness of the tubular body (rim) may be zero in some regions, meaning that the tubular body includes holes or windows, or comprises a frame.

Regions of different wall thickness may result in different regions of the airflow passageway having different diameters or cross-sectional shapes. For example, in some variations the device has a tubular body forming a passageway, and the inner wall of the passageway includes a step or ledge along the inner wall of the passageway. In one example, the outer diameter (OD) of the tubular body is uniform while the inner diameter (ID) has at least two different measures. As described in more detail below, this ledge or step within the passageway may form a valve seal surface by providing a surface on which a valve (e.g., a flap valve) may abut or lie against when in the closed position.

In variations having a tubular body (i.e., rim), the tubular body may have any appropriate cross-sectional area. For example, a rim configured as a tubular body may have an elliptical cross-section through its length that is shaped similarly to that of most subjects' nares. This shape may help maximize the cross-sectional size of the passage while maintaining comfort. In any of the variations described herein, the passageway may comprise nay appropriate cross-sectional shape or shapes, such as circular, polygonal, teardrop, or other asymmetric shapes.

In some versions, the respiratory device does not include a separate rim forming the passageway. For example, the airflow passageway of the respiratory device may be a passageway through a holdfast.

The devices described herein typically include an airflow resistor configured as a flap valve. An airflow resistor is typically positioned in communication with the airflow passageway, so that at least some of the air flowing through the passageway passes the airflow resistor. Thus, an airflow resistor modulates, alters, varies, or keeps constant the amount of resistance, the degree of airflow, or the pressure differential across the device or through a passageway in the device. In some versions, the airflow resistor inhibits airflow more greatly in one direction than the opposite direction. Thus, the airflow resistor may regulate airflow to and from the lungs. Some versions of the device have a greater resistance to exhalation than to inhalation during use.

In some versions of the respiratory device, the airflow resistor comprises a valve that does not appreciably impede airflow in a certain direction (e.g., inspiration), and that partially or completely impedes airflow in the other direction (e.g., expiration). In some embodiments, the valve allows for an expiratory obstruction to be relieved if a certain degree of airflow or pressure differential across the device is achieved, as might be the case with coughing or nose blowing. For example, in some embodiments, the valve comprises a flap made of a shape memory or deformable material (e.g., an elastic material); when the pressure differential across the valve (the expiratory airflow pressure) is large enough, the flap bends upon itself, thereby relieving the obstruction. This may be important during coughing and may also facilitate the clearance of mucous and other substances during coughing. After the cough, the flap returns to its original, non-bent conformation. Alternatively, embodiments that allow for relief of expiratory obstruction if a certain airflow or pressure differential across the device is achieved may act as a PEEP valve where PEEP refers to positive end expiratory pressure.

Examples of different types of airflow resistors have been previously described (e.g., in U.S. patent application Ser. No. 11/298,640), and may be shown in some of the figures below. However, valve type airflow resistors, and particularly "flap valve" resistors are of particularly interest. In general the airflow resistor is capable of altering the resistance of air passing through an air passageway during expiration and/or inspiration, for example by selectively increasing the resistance of air flow in one direction more than in the opposite direction. Multiple airflow resistors may also be used, which may include combinations of different types of airflow resistors (including multiple flap valves).

A flap valve is an airflow resistor having one or more flaps or leaves that may move to block or open a passageway. The flap may be made of a stiff or flexible material, or some combination thereof. In some variations, the flap valve includes a stiff region of the valve, which may help give the flap support. In some variations, the flap comprises a polymeric material, as described below. The flap valve may be biased (e.g., in an open or a closed position) or it may be unbiased. A bias element such as a spring may be used, or the flap may be made of a material that has elastomeric properties that bias the valve in a particular position. A biased valve is a valve that tends to remain in a particular position (e.g., flat, bent, open, closed, etc.) when at rest. In some variations, the flap valve includes a flap made of an elastomeric material such as silicone. In this variation, the flap comprises a sheet of silicone that is cut (e.g., laser cut, dye cut, etc.) so that the flap (or flaps) can cover the opening of the device passageway when the valve is closed, and may bend to expose the passageway to airflow when the valve is opened. The flaps may be secured to the wall of the passageway (e.g., to the tubular body). The flap valve (or other variations of the airflow resistor) may also be used with additional components. For example, respiratory devices may include an airflow resistor seal surface (valve seal surface), an airflow resistor support (valve support), and/or an airflow resistor aligner (valve aligner).

A flap of a flap valve may be continuously flexible. For example, a flap may be made of a relatively flexible material such as silicone (or other rubbers). Although these flaps may be relatively stiff (e.g., depending on the shape, thickness, etc.), they are typically bendable over the majority of the movable portion of the flap. In using a continuously flexible flap as part of the flap valve, it may also be useful to include a support for the flap (e.g., a flap valve support), as described in greater detail below. In addition, nasal respiratory devices may be configured so that the flap is protected within at least a portion of the device during operation of the device (e.g., both when the flap is open and when it is closed), preventing interfering contact with the subject's nose.

The flap valve may be any appropriate shape, particularly shapes in which the passageway may be blocked or at least partially occluded. The flap is typically flat, though it may be any appropriate thickness, and the valve may have any appropriate surface area and surface shape. As described further below, the passageway may have an elliptical or irregular cross-sectional shape (e.g., when looking into the passageway from one end of the valve). For example, when the device is inserted into the nose, the passageway may have a substantially elliptical cross-sectional profile. Thus, the flap valve may be substantially elliptical in shape (e.g., enface shape) so that it may fit within the passageway. The flap may therefore be substantially flat, but include an elliptical (including oval), polygonal, or asymmetric (including tear-drop shaped) cross-section.

A flap may be thin enough to allow the entire flap to flex or bend, curving all along its length. In this variation, the flap may move to provide a large opening even when only a very small differential pressure is applied across the face of the valve. Thin, highly flexible flap valves may be particularly useful when used in conjunction with a support member, as described further below.

A flap valve may also have any appropriate dimensions, (e.g., thickness and surface area), so that it may block the passageway of a respiratory device sufficiently to provide a desired resistance to exhalation and/or inhalation during use. For example, the flap valve may be a non-circular flap valve (e.g., an elliptical flap valve), in which the ratio of the long axis of the flap valve profile to the short axis of the flap valve profile is between about 1.2:1 and about 3:1. In one variation, the long axis of the non-circular profile is between about 8 mm and about 20 mm long.

The respiratory devices described herein may also include airflow resistor seals, airflow resistor supports, valve aligners, and/or valve locks. For example, these devices may include a valve seal surface that seats the airflow resistor when it is in the closed position, permitting it to "seal." As used herein, a valve seal surface does not have to provide a tight seal. A valve seal surface may be provided so that the airflow resistor (e.g., flap valve) operates in a predictable manner, for example, obstructing the airflow through the passage to approximately consistent levels when in the closed configuration. A valve seal surface may be a seat or surface against which the valve portion of the airflow resistor contacts when closed. When the airflow resistor is a flap valve, the valve seal typically comprises a valve seal surface that is a flat surface against which the flap valve, and particularly the periphery of the flap valve, rests when the flap valve is closed. As described in the examples below, and shown in FIGS. 30a-30b, the valve seal surface for a flap valve may comprise a lip or ridge around the inner diameter of the passageway (e.g., the rim or tubular body forming the passageway).

A valve seal surface may comprise any appropriate surface for seating the valve. For example, the valve seal surface may comprise a hard surface. In some variations, the valve seal surface comprises a cushioned or compliant material which may help prevent damage to the valve. The valve seal surface is typically smooth. The valve seal surface may extend within the passageway. The surface of the valve seal surface may be adapted to seat the edge of the flap valve. For example, the valve seal surface may include a flap seating surface that is parallel with the flap (when it is in the closed position). The valve seal surface may also support the valve, particularly around the perimeter of the flap. A valve seal surface may be used as (or in addition to) a flap valve support.

In some variations, the valve seal surface is not flat. For example, the valve seal surface may be ridged, notched, or sinuous. Such surfaces may help control the seating of a flap valve in order to delay the complete closure of the flap valve. For example, a flexible flap valve may seal with a non-flat surface more gradually than it would with a flat surface when exposed to the same differential pressure across the flap. Delaying closure and seal of the flap valve to later in the exhalation cycle may be beneficial. For example, it may make inhalation initially easier. Also, as described further below, the valve seal surface may comprise a leak path. For example, the valve seal surface may include one or more passageways (e.g., missing regions) which do not permit sealing with the flap valve.

A respiratory device may include a valve support. This airflow resistor valve support (specifically referred to as a flap support or a flap valve support) prevents the flap of the flap valve from improper operation. For example, a valve support appropriate for a flap valve may prevent the flap(s) of the flap valve from collapsing when in the closed position or extending past the closed position. For example, when a flap valve is configured to open by moving the flap (or flaps) distally, a valve support may be located adjacent to the flap valve proximally to restrict proximal motion of the flaps. The flap valve support may be configured to contact (or support) any region of the flap, but particularly the more central portions of the flap. For example, a flap support may support the appropriate center of the region of the flap that moves.

A flap valve support may be a bar, post, notch, mesh, web, cable, or the like, and typically projects into the passageway behind a portion of the valve (e.g., the flap) to provide support. The flap valve support may be stiff or flexible. A flap valve support typically supports the moving member of the flap or flaps in one or more positions. Flap valve supports may be used with any airflow resistor. When used with a flap valve, the flap valve support may prevent the flap from opening during one half of the respiratory cycle, despite large pressures. For example, in one variation of a device including a thin flap valve, the valve is configured so that the flap bends easily in the distal direction to "open" the valve and expose the device passageway during inhalation. The flap may then return to the unbent position to close over the passageway during exhalation. Pressure from the subject's lungs during exhalation pushes against the flap. A flap valve support located adjacent and proximally to the flap may prevent this pressure from bending or buckling the flap proximally and thereby opening the valve during exhalation.

Figure 27:
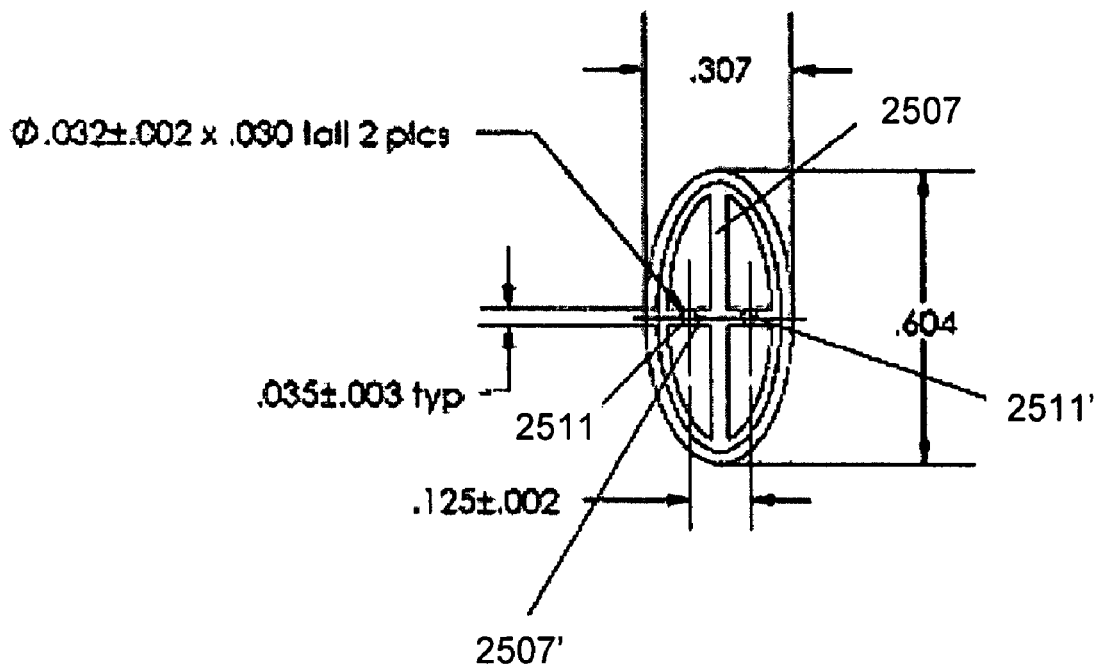

In some variations, a valve support includes one or more crossbars. As described further below, FIG. 27 illustrates a valve support having two crossbars. In general a valve support is located within the passageway, and presents a profile that only minimally affects the airflow through the passageway. A valve support may span the entire diameter of the passageway, or only a portion of the passageway. In some variations, the valve support is a beam or crosspiece that spans the passageway of the respiratory device.

Figure 30A:
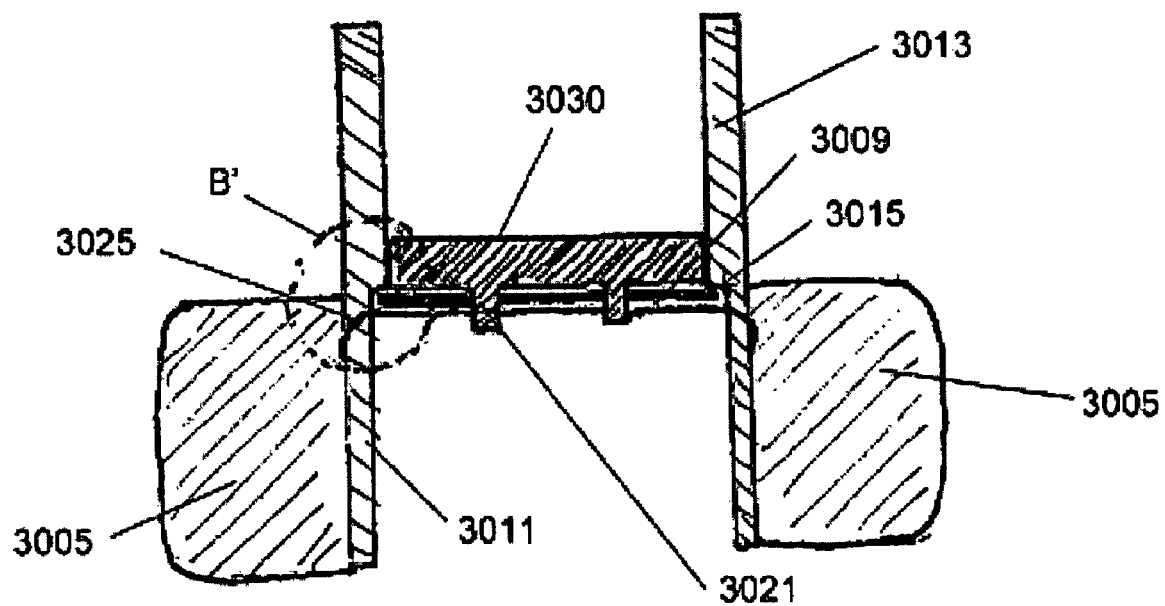
FIGS. 30a and 30b show cross-sectional views of the respiratory device of FIG. 29.

A respiratory device may also include a valve aligner. A valve aligner may be used to align the airflow resistor within the passageway, particularly the movable portion of the airflow resistor. Aligning the airflow resistor may make the movement of the airflow resistor predictable. A valve aligner may also secure the valve within the passageway. For example, a flap valve may be used with one or more valve aligners so that the flaps open and close without contacting the sides of the passageway, or otherwise interfering with portions of the respiratory device. The valve aligner may be used to hold the valve in place in conjunction with a fulcrum support, as described further below. A valve aligner may comprise a post, a notch, a knob, a socket, etc. In general, the valve aligner mates with a portion of the valve. For example, a flap of a flap valve may be positioned within the passageway by mating with a post (valve aligner). The post may pass through a hole in the flap valve that holds the valve in the passageway in the correct position. Two posts, offset from each other, or a non circular cross-section post may be used to orient the flap valve within the passageway. An example of a valve aligner is shown in FIG. 30a.

A respiratory device may also include a valve lock (e.g., a flap valve lock) for securing the movable portion of a valve (e.g., the flap portion of a flap valve) within the passageway of the device. A flap valve lock may enhance the safety of the respiratory devices by preventing the flap from detaching from the device during operation. A flap valve lock may be configured to prevent the flap portion of a flap valve from separating from the device even when the flap valve is exposed to large (e.g., physiologically large) pressures applied to the device. In most applications the flap valve lock prevents the flap valve from separating in the distal direction within the passageway, since the valve support typically restrains the flap valve in the proximal direction. Of course, the distal and proximal orientations of the device may be reversed, as described herein.

A flap valve lock typically comprises a restraining member such as a pin, a cord (e.g., a fiber, thread, strap, etc.), a button, or the like, that prevents the flap from separating from the device. In some variations, the flap valve lock contacts the flap. For example, the flap valve lock may be a cord or pin that passes through a region of the flap. In some variations, the flap valve lock is not connected directly to the flap, but prevents the flap from separating from the device only when the flap moves into contact with the flap valve lock. In variations of the device in which a valve aligner is used, a valve lock may be used in conjunction with the valve aligner to prevent the flap from disengaging from the valve aligner. For example, if the valve aligner is a post passing through the flap, a valve lock may be a blocking element (e.g., a knob, button, cap, etc.) at the end of the valve aligner preventing the flap from disengaging from the respiratory device. If the flap moves down the valve aligner too far in the distal direction, the valve lock prevents it from separating from the valve aligner, and keeps the flap substantially within the passageway.

Figure 31A:
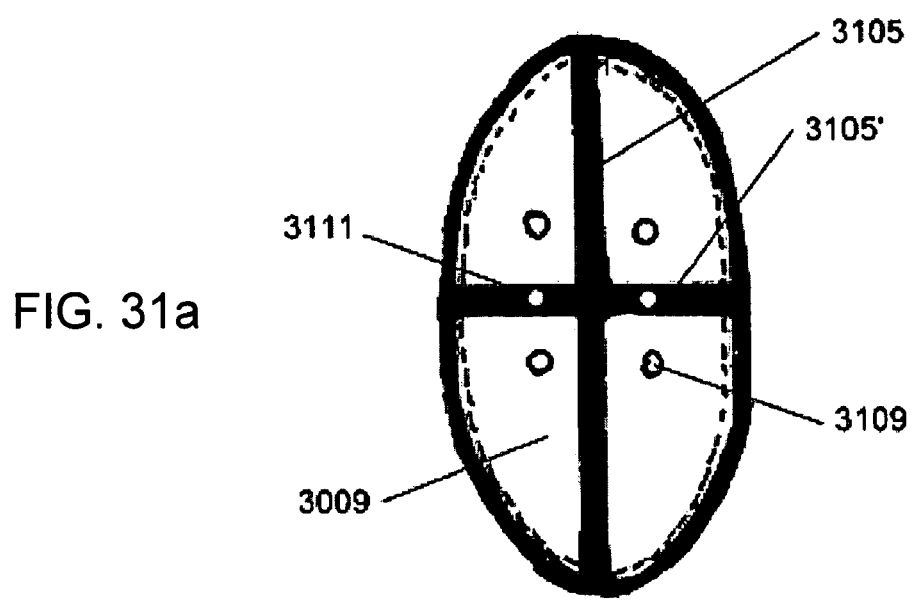
FIG. 31a shows one example of a flap valve seated in a respiratory device.

The respiratory devices described herein may also include one or more leak paths. A leak path allows air to flow through or past the respiratory device even when the airflow resistor is closed. A leak path may be included as part of any portion of the device, including the holdfast, the rim (e.g., the tubular body), or the airflow resistor. The sizes, locations and distributions of the leak path(s) may be chosen to permit a desired amount of airflow through the device at a known pressure and/or flow rate. In particular, the leak path may be incorporated as part of an airflow resistor. For example, the leak path may be one or more holes or channels through a flap. A leak path may also be included as a notch or region of the flap 3121 as shown in FIG. 31a. In FIG. 31a, the airflow resistors are shown as portions of the periphery of the flap valves which do not mate with a valve seal, allowing air to flow past the flap valve even when the valve is in the closed position. In some variations, the leak path is not included as part of the valve.

As mentioned above, a flap valve may include one or more passages or holes through which air can pass even when the flap valve is closed. These leak paths may be chosen so that they maintain a predetermined pressure across the closed airflow resistor when air is flowing through or around the device at a known flow rate. For example, in a flap valve, leak paths (e.g., holes) may be sized so that when the device is exposed to a constant flow rate of 100 ml/sec, and the valve is in the closed position, the pressure across the flap valve is between about 0.5 and 20 cm of $H_2O$, or between 3 and 15 cm of $H_2O$. In one variation the flap valve includes four holes having a diameter of approximately 0.03 inches (±0.01), resulting in a pressure of approximately 8 cm $H_2O$ when exposed to 100 ml/sec airflow. Any appropriate number and size leak paths may be included so that the differential pressure between inhalation and exhalation may be controlled. This is described in more detail below.

In general, the respiratory devices described herein affect both the inspiratory and expiratory resistances in subjects wearing the devices. In some variations, resistance during inspiration is affected as little as possible, and resistance on expiration is controlled to allow a leak of a specified amount of airflow. The resistance to airflow in either inspiration or expiration may be understood in terms of back-pressures at a given flow rate. Back pressure can be defined as the differential pressure across the valve, and is positive on the side of the valve from which the air is flowing. For example, the back pressure during inspiration may be <1 cm $H_2O$, or more preferably, less than 0.3 cm $H_2O$, and most preferably less than 0.2 cm $H_2O$, when measured at a flow rate of 100 ml/sec. On expiration, it may be desirable to have a back pressure of between about 0.1 to about 20 cm $H_2O$ (or more preferably between 3 and 15 cm $H_2O$) when measured at a flow rate of 100 ml l/sec (when the device is configured for both nostrils). Both the back pressure on inspiration and back pressure on exhalation are present in the same device. The flow rates provided here are in reference to a nasal device having one or more airflow resistors, and typically refer to a pair of airflow resistors (e.g., one airflow resistor per nostril). When referring to a single nostril device, the differential pressure (back pressure) is measured at a flow rate that is typically 50 ml/sec. Oral devices may use a corresponding flow rate.

The total leak path is the sum of the leak paths through the device (e.g., the sum of all of the unregulated flow past the device when properly worn by a subject). The devices described herein may have a back pressure to inspiration that is between about 0.01 and about 5 cm $H_2O$, or between about 0.01 and about 2 cm $H_2O$, or between about 0.1 and about 2 cm $H_2O$, or less than about 1 cm $H_2O$. This gives a resistance to inspiration (in cm $H_2O$/ml/sec), when measured at a flow rate of 100 ml/sec, of between about 0.0001 cm $H_2O$/ml/sec to about 0.05 cm $H_2O$/ml/sec, or between about 0.0001 cm $H_2O$/ml/sec to about 0.02 cm $H_2O$/ml/sec, or between about 0.001 cm $H_2O$/ml/sec to about 0.02 cm $H_2O$/ml/sec, or less than about 0.01 cm $H_2O$/ml/sec. The devices described herein may have a back pressure during exhalation that is between about 0.1 cm $H_2O$ and about 25 cm $H_2O$, between about 1 cm $H_2O$ and about 25 cm $H_2O$, between about 2 cm $H_2O$ and about 20 cm $H_2O$, between about 3 cm $H_2O$ and about 20 cm H2O, and between about 3 cm $H_2O$ and about 15 cm $H_2O$. This gives a resistance to expiration (in cm $H_2O$/ml/sec), when measured at a flow rate of 100 ml/sec, of between about 0.001 cm $H_2O$/ml/sec and about 0.25 cm $H_2O$/ml/sec, or between about 0.01 cm $H_2O$/ml/sec and about 0.25 cm $H_2O$/ml/sec, or between about 0.02 cm $H_2O$/ml/sec and about 0.2 cm $H_2O$/ml/sec, or between about 0.03 cm $H_2O$/ml/sec and about 0.2 cm $H_2O$/ml/sec, or between about 0.03 cm $H_2O$/ml/sec and about 0.15 cm $H_2O$/ml/sec.

The back pressure for inspiration and for expiration is typically determined by the configuration of the leak paths and airflow resistor. For example, in a device having a flap valve, when the flap valve is closed during expiration, the back pressure for expiration is typically a function of the leak paths through or around the device, which may include leak paths through the flap as well as leak paths through other portions of the device, such as the body (e.g., rim) and the holdfast. In the same example, when the flap valve is open during inhalation, the back pressure for inspiration may be a function of the open passageway through the device (regulated by the flap valve) plus any leak paths located on non-flap regions of the device. Any leak paths on the flap typically do not contribute to the back pressure for inspiration, since (in this example) the passageway through the device that is controlled by the flap valve is open. Flow through the leak path is typically determined by the size, shape and location of the leak paths (as well as the number of leak paths).

As described above, a leak path may be located anywhere on the device, including the movable portion of the airflow resistor (e.g., the flap of a flap valve), and on portions of the device that are not the airflow resistor (e.g., the holdfast or the body). Leak paths formed through non-airflow resistor (e.g., non-flap) portions of the device may also be particularly beneficial because they may be quieter and/or more predictable than leak paths through movable portions of the airflow resistor. For example, a leak path through a thin flap (particularly a silicone flap) may vibrate when air flows through it.

A respiratory device may further comprise a holdfast for releasably securing the device in communication with a nasal and/or oral cavity. The holdfast may facilitate the positioning and securing of the device in a desired location, such as over or within, or both over and within, or at least partially within a respiratory orifice. In particular, the holdfast may allow the device to be anchored, positioned, and/or stabilized in any location that is subject to respiratory airflow such as a respiratory cavity.

Examples of respiratory cavities include nasal and oral cavities. Nasal cavities may comprise the nostrils, nares or nasal chambers, limen, vestibule, greater alar cartilage, alar fibrofatty tissue, lateral nasal cartilage, agger nasi, floor of the nasal cavity, turbinates, sinuses (frontal, ethmoid, sphenoid, and maxillary), and nasal septum. The term "nasal cavity" may refer to any sub-region of the Nasal Fossa (e.g., a single nostril, nare, or nasal chamber).

In some versions, the holdfast may also secure a seal between the respiratory device and the respiratory airway, so that at least some of the air exchanged between the outside of the subject and the respiratory airway must pass through the respiratory device. In some versions, the holdfast seals the device in communication with a respiratory cavity completely, so that all air through that respiratory opening must be exchanged through the device. In some versions, the holdfast seal is incomplete, so that only some of the air exchanged between the subject and the external environment passes through the device. As used herein, "air" may be air from the environment external to the subject, or it may be any respiratory gas (e.g., pure or mixed oxygen, $CO_2$, heliox, or other gas mixtures provided to the user). In some versions, the holdfast may comprise an anchor or anchor region.

In some variations, the device is to be placed by the subject or the healthcare provider in or around (or both) the nasal cavity. Holdfasts appropriate for nasal cavities may secure the device in position within a nasal cavity (e.g., through one or both nostrils) or against surrounding structures. The holdfast may comprise a shape, surface or material that secures the device in communication with a nasal cavity. For example, the holdfast may comprise a cylindrical shape that allows the device to fit securely or snugly within a nostril. The outer surface of the device may be formed by a holdfast including an adhesive material. In addition to holding the device in place, the holdfast may also partially or completely seal the device in communication with the nasal cavity. The holdfast may comprise insertive and/or non-insertive mechanisms. In some versions, the holdfast comprises a mechanical connection between the device and the user, such as clips, straps, and the like.

The holdfast may be formed from a soft or compliant material that provides a seal, and may enhance subject comfort. Furthermore, compliant materials may reduce the likelihood that the device cuts off blood flow to the part of the respiratory cavity and surrounding regions (mouth or nose) to which the device is anchored. This compliant material may be one of a variety of materials including, but not limited to, plastic, polymers, cloth, foamed, spongy, or shape memory materials. Shape materials include any that have a preferred conformation, and after being deformed or otherwise deflected or altered in shape, have tendency to return to a preferred conformation. Soft shape memory materials may include, but are not limited to, urethane, polyurethane, sponge, and others (including "foamed" versions of these or other materials). Alternatively, the holdfast may not be soft or compliant and may instead be a rigid structure that interfaces directly with the respiratory orifice. For example, in versions of the respiratory device configured to be used at least partially within a nasal cavity, it is understood that the device may fit completely within a nostril (or both nostrils), or may project out of the nostril, depending on the particular embodiment. In some cases, the device may be placed high enough within the nasal cavity so that it cannot be seen within the nostril. In some embodiments the device may be located completely outside of the nose, for example, in some versions the holdfast has a shape that conforms to the outside surface of the nose. Thus, the holdfast may comprise one or more straps, bands, or the like to ensure an adequate fit and/or seal maintaining the device in communication with the nasal cavity. In another embodiment the holdfast may comprise one or more projections that are inserted within the nostrils. In some versions, a device may be placed at least partially in both nostrils, and may comprise a bifurcated passageway or two passageways that the holdfast places in communication with the nasal cavity through each nostril. In this case, the inspiratory and/or expiratory airflow to and from the lungs may be regulated through each nostril separately or together. In some versions, separate devices may be placed at least partially in each nostril, and may be connected to each other and/or to the subject using a clip, tether, strap, band, chain, string, or the like. Such a system would facilitate subsequent removal of the device and make migration of the devices deeper into the nasal cavity less likely. Finally, in some devices, an adhesive flap may be present to help attach the device to the inside or outside of the nose (including the nostrils), to the oral cavity, to the neck, or to the face. The use of an adhesive or any other means may prevent the inadvertent or otherwise undesired removal of the devices during sleep.

The holdfast portion of a respiratory device may also be shaped to fit within the subject's anatomy to secure the device in place and/or to prevent leakage of airflow around the device. For example, the holdfast may be shaped to fit within the widening of the nasal cavity immediately inside the nares (opening of the nostril). As mentioned above, the holdfast may conform to the walls of a portion of the nasal cavity both to hold the device within the nose, and also to prevent substantial leak of air around the device when worn in the nose. Materials such as foams (e.g., foamed polyurethane) may be particularly useful for this purpose, since these materials may be readily compressed for insertion and rapidly expand within the nasal cavity to secure the device in place.

A holdfast may be attached to a respiratory device. For example, a holdfast may be attached to a rim. In one variation, the holdfast is connected to the outer surface of the tubular body. A holdfast may be glued, taped, stitched, welded, or otherwise connected to the rim of a respiration device. In some variations the holdfast circumferentially surrounds at least a portion of a rim. For example, in one variation the distal end of the tubular body (e.g., rim) of the device is ensheathed by a holdfast of foamed material. In some variations, the holdfast thickness is substantially uniform along most or the entire periphery of the device. In some variations, it may have variable thickness, for example it may be thicker or thinner at the long ends of the device. In other cases, the holdfast thickness may be either symmetrically or asymmetrically distributed. Similarly, the height and length of the foam forming a holdfast may also be uniform or non-uniform, symmetrically or asymmetrically distributed.

Figure 29:
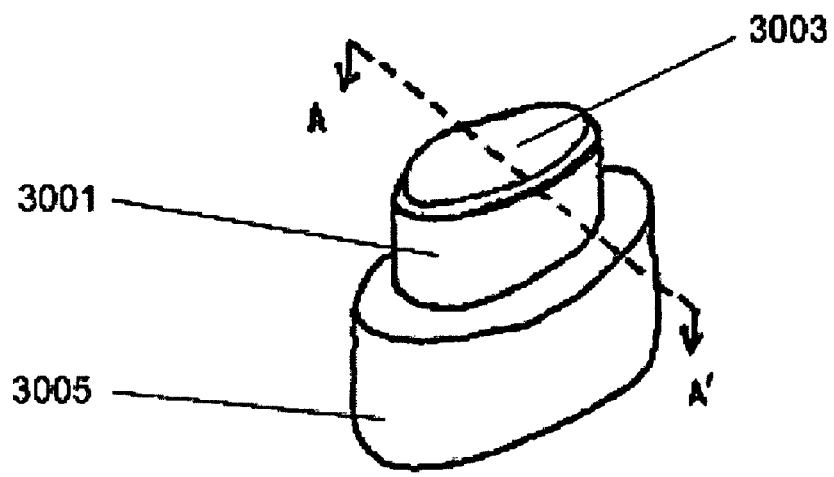
FIG. 29 shows a perspective view of one variation of a respiratory device as described herein.

A holdfast may be thicker in some regions than in other regions. For example, the cross-sectional profile of the holdfast (e.g., the profile though the long axis of a respiratory device including a holdfast) may be thicker in some places than in others. In some variations, e.g., when the tubular body or passageway of the device has an elliptical profile (cross-sectional profile) as shown in FIG. 29, the holdfast in communication with the tubular body is thicker near the long axis of the elliptical profile of the tubular body than at the short axis of the tubular body. In some variations, the thickness of the holdfast around the profile of the tubular body cross-section is related to the diameter of the passageway through the device. For example, the thickness of the holdfast at any point outside of the passageway may be between about 0.2 times and about 2 times the distance from the center of the passageway to the outer edge of the tubular body around the radius of the passageway. On an exemplary device having a tubular body with an elliptical profile, the holdfast may be between about 0.8 mm and about 8 mm thick at the long axis of the elliptical cross-section of the tubular body, and between about 0.4 mm and about 4 mm thick at the short axis of the elliptical cross-section of the tubular body.

The device may be removably secured by a holdfast, meaning that the device may be inserted into the subject's nasal cavity for some amount of time, and then removed. For example, a removable holdfast exerts sufficient pressure on the nostril walls (e.g., within the nasal cavity) to hold the device in position without harming the subject, or producing too much discomfort. The device may be used continuously for an appropriate time period (e.g., overnight, such as 6-8 hours). Thus, the holdfast does not generally need to be secured more permanently. The holdfast material properties and shape typically lend themselves to easy, fast, and pain-free insertion and removal. Thus, as described herein, the holdfast may be a compressible/expandable foam material. The shape and size of the holdfast may also be chosen to appropriately secure the device within a subject's nasal cavity comfortably. For example, the foam may have compression properties that allow it to be readily compressed (for insertion into the nasal cavity), but expand to fit the cavity quickly once inserted. The holdfast may also have a thickness and width sufficient to fit snugly but comfortably within the subject's (including an 'average' subject or range of different subject sizes) nasal cavity. In some variations, the foam thickness is not uniform. For example, in some variations, the ends of the holdfast region comprise a foam that is thicker at the ends than in the middle, which may allow the device to fit noses which are longer and narrower.

Respiratory devices may be made from any appropriate material or materials. In certain embodiments, the devices include a shape memory element or elements, as part of the holdfast, in the airflow resistor, or in giving form to the passageway. Any convenient shape memory material that provides for flexibility and resumption of configuration following removal of applied force may be employed in these embodiments. For example, shape memory alloys may be used. A variety of shape memory alloys are known, including those described in U.S. Pat. Nos.: 5,876,434; 5,797,920; 5,782,896; 5,763,979; 5,562,641; 5,459,544; 5,415,660; 5,092,781; 4,984,581; the disclosures of which are herein incorporated by reference in their entirety. The shape memory alloy that is employed should generally be a biocompatible alloy. Biocompatible alloys may include nickel-titanium (NiTi) shape memory alloys sold under the Nitinol™ name by Memry Corporation (Brookfield, Conn.). Also of interest are spring steel and shape memory polymeric or plastic materials, such as polypropylene, polyethylene, etc.

Rubber and polymeric materials may also be used, particularly for the holdfast, rim, or airflow resistor. Injection moldable materials such as polyether block amide (e.g., PEBAX®), and the like may be used. Materials which may be used include: latex, polyethylene, polypropylene, polystyrene, polyvinyl chloride, polyvinylidene chloride, polyvinyl acetate, polyacrylate, styrene-butadiene copolymer, chlorinated polyethylene, polyvinylidene fluoride, ethylene-vinyl acetate copolymer, ethylene-vinyl acetate-vinyl chloride-acrylate copolymer, ethylene-vinyl acetate-acrylate copolymer, ethylene-vinyl acetate-vinyl chloride copolymer, nylon, acrylonitrile-butadiene copolymer, polyacrylonitrile, polyvinyl chloride, polychloroprene, polybutadiene, thermoplastic polyimide, polyacetal, polyphenylene sulfide, polycarbonate, thermoplastic polyurethane, thermoplastic resins, thermosetting resins, natural rubbers, synthetic rubbers (such as a chloroprene rubber, styrene butadiene rubber, nitrile-butadiene rubber, and ethylene-propylene-diene terpolymer copolymer, silicone rubbers, fluoride rubbers, and acrylic rubbers), elastomers (such as a soft urethane, water-blown polyurethane), and thermosetting resins (such as a hard urethane, phenolic resins, and a melamine resins).

Biocompatible materials may be used, particularly for those portions of the device (e.g., the holdfast) which may contact a user. In addition to some of the materials described above, the biocompatible materials may also include a biocompatible polymer and/or elastomer. Suitable biocompatible polymers may include materials such as: a homopolymer and copolymers of vinyl acetate (such as ethylene vinyl acetate copolymer and polyvinylchloride copolymers), a homopolymer and copolymers of acrylates (such as polypropylene, polymethylmethacrylate, polyethylmethacrylate, polymethacrylate, ethylene glycol dimethacrylate, ethylene dimethacrylate and hydroxymethyl methacrylate, and the like), polyvinylpyrrolidone, 2-pyrrolidone, polyacrylonitrile butadiene, polyamides, fluoropolymers (such as polytetrafluoroethylene and polyvinyl fluoride), a homopolymer and copolymers of styrene acrylonitrile, cellulose acetate, a homopolymer and copolymers of acrylonitrile butadiene styrene, polymethylpentene, polysulfones polyimides, polyisobutylene, polymethylstyrene and other similar compounds known to those skilled in the art.

A respiratory device may be oriented in any direction. For example, in some embodiments, the airflow resistor comprises a flap valve that is oriented such that the flap(s) are in a closed position during expiration and in an open position during inspiration, so that the airflow resistor increases resistance to expiration, and has a relatively lower or negligible resistance to inspiration. However, these devices can be oriented in the opposite direction as well, so that the device offers increased resistance to inspiration and decreased resistance to expiration. Such orientation may be used for a variety of pulmonary, cardiac, inflammatory, neurologic, or other disorders that might benefit from such changes in resistance and its subsequent changes to intra-thoracic and airway pressures. This version of the device may be structurally identical to other embodiments described elsewhere in this application. In some versions, the respiratory device is reversible, so that it may be used in either orientation by the user (e.g., to increase the resistance of inspiration relative to expiration in one orientation, or to increase the resistance of expiration relative to inspiration in another orientation). In one variation, a respiratory device may be used in one nostril in an opposite orientation to a respiratory device in the other nostril, which may alternate through which nostril resistive inspiration or expiration occurs.

In some versions, the respiratory device is shaped so that the direction of the airflow resistor is immediately evident. For example, the respiratory device may be of a different shape or size on one end, or may include a visual indication. In one version, the respiratory device may be shaped so that it fits securely into a respiratory orifice only in one orientation (e.g., so that the airflow resistor inhibits the expiration more than it inhibits inhalation). For example, a flange or other mechanical stop may be used to insure proper orientation, while simultaneously preventing migration of the device further into the respiratory orifice.

In many embodiments, the device provides some level of resistance to expiration. It may be preferable to have little if any effect on resistance to inspiration, though in some cases, some degree of inspiratory restriction may be beneficial. In some versions of the device, both inspiration and expiration may be inhibited by the airflow resistor.

The device may also be adapted for comfort. Any device placed either in or around the oral cavity or in or around the nose should not cause undue pain or discomfort, and if possible, should not be noticeable by the subject. Thus, the holdfast may be shaped to conform to the attachment site in or around the respiratory orifice. In some versions, the holdfast comprises a flexible or shapeable material (e.g., a foam or other soft shape-memory material). In some versions, the entire respiratory device comprises a soft material.

When using devices that feature a foam on the portion of the device that fits within or otherwise communicates with the inside of a nostril, the device may be inserted by the subject or healthcare provider foam end first. It may be helpful to insert a corner of the device into the nostril and then rotate the device into place. The device may then be gently pulled outward (without removing the device from the nostril) so that it rests in the correct position and provides a seal between the periphery of the device and the nasal cavity or nostril.

The user may be instructed to breathe through his/her/its mouth or nose, whichever is more comfortable. If the device is going to be worn by a subject during sleep, the user may be instructed to breathe primarily or relatively primarily through his mouth while he is still awake. This may make the sensation of expiratory resistance and pressure easier to tolerate. It is expected that when the subject goes to sleep, he will revert primarily or at least partially to nose breathing, thus promoting the beneficial effects of the device. The subject devices may also be used with any commercially available device that promotes closure of the mouth during sleep, including but not limited to straps, mouthguards, tape and the like.

In some cases, a nasal cannula or other means of monitoring nasal airflow (such as a thermistor) may be attached, fixed, or non-fixably positioned within or near the device to allow various diagnostic parameters to be measured. In some cases, the nasal cannula or other diagnostic device may be held in place with tape (on the face for example, near the chin or cheek). By attaching the diagnostic device to the device, it is less likely that inadvertent or undesired motion will shift or displace the device while sleeping or otherwise during use. In some cases, the subject device may be extended or otherwise altered or changed to allow the placement of the nasal cannula.

In other cases, an intranasal pressure probe or sensor may be placed beyond the device (deeper within the nasal cavity or nostril) to provide a pressure reading for the airways, nose, and other respiratory pathways.

Furthermore, the device may be adapted so that it is more or less visible to others. In some cases, the device may be configured to be placed high enough within the nostrils to make it difficult for others to see. Furthermore, the device may be of any color and/or pattern that help to camouflage it. In other versions, it may be useful to include colors and patterns that stand out, including ones that are fluorescent or otherwise offer increased visibility during the night or other setting where ambient light is reduced.

In some versions, the respiratory device may be "one size fits all", so that it may be used with any subject (or any subject of approximately the same size), despite differences in shapes and sizes of their nose/nostrils, oral cavity, teeth and other relevant anatomic features. In one version, the devices may conform to a range of sizes, for example "small," "medium," and "large" (or any other appropriate range, such as, e.g., a numerical range). Alternatively, the devices may involve a custom fit of the device or devices to the subject.

Custom fitting may improve subject comfort and potentially improve performance by improving the seal between the device and the subject's oral cavity, mouth, nasal cavity and nostrils, for example. In some versions, custom fitting may involve the placement of a device in warm or cold liquid or air with subsequent placement in the subject's nose or mouth. This process is meant to "prime" the materials in the device (e.g., particularly the materials of the holdfast), so that when the holdfast is secured to the subject, the device permanently assumes a shape or configuration corresponding to a portion of the subjects anatomy.

In some cases, the device may be over the counter (OTC) and in other cases, it may require a prescription. Some possible indications for the device will include but not be limited to sleep apnea, snoring and upper airway resistance syndrome. In other cases, the device may be used to improve athletic performance, heart or lung function, or improve oxygenation. In some cases, the devices will be reusable. In some cases, the devices will be disposable after one or more uses. The devices may be modular; for example, at least one component or subassembly of the device may be reusable and at least one component or subassembly may be disposable.

As described above, the device may include one or more holes or air leak paths even in the closed position, so that some air may pass through the device even if the holdfast forms a relatively tight seal with the nasal cavity. For example, the airflow resistor (e.g., flap valve) may include one or more holes providing an air leak path. The size of the holes may be configured to allow a predetermined rate of airflow through the holes when a certain pressure is applied (e.g., by the user's breathing). For example holes may be small (e.g., having diameters of 0.030 inches ±0.010 inches). In some variations, multiple holes are used. The total leak through the leak path may be the sum of the leak through all of the leak paths (e.g., holes). The size and number of leak paths may be chosen based on the desired I:E ratio, as described below.

Figure 31B:
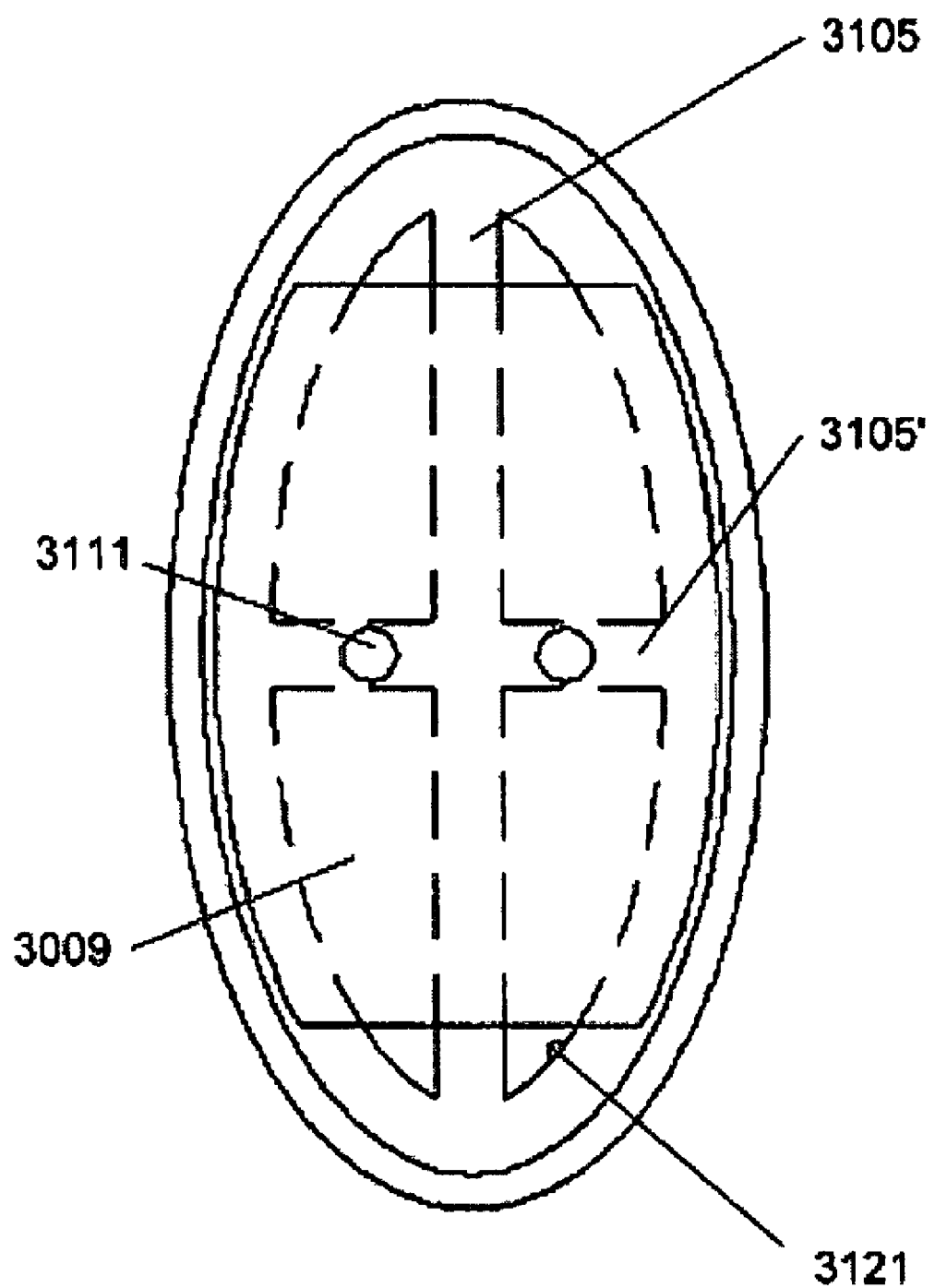
FIG. 31b shows another example of a flap valve.

A leak path (e.g., a hole) may be on any appropriate region of the device, on the holdfast, on the rim, or on some combination of these. In some variations, the leak path may be provided by removing a portion of the airflow resistor, as illustrated in FIG. 31b. For example, a portion of the edge of a flap valve may be missing, providing a leak path, or the flap valve may include one or more holes. In variations in which the holdfast comprises a foamed material, the foam itself may provide a leak path.

Figure 32A:
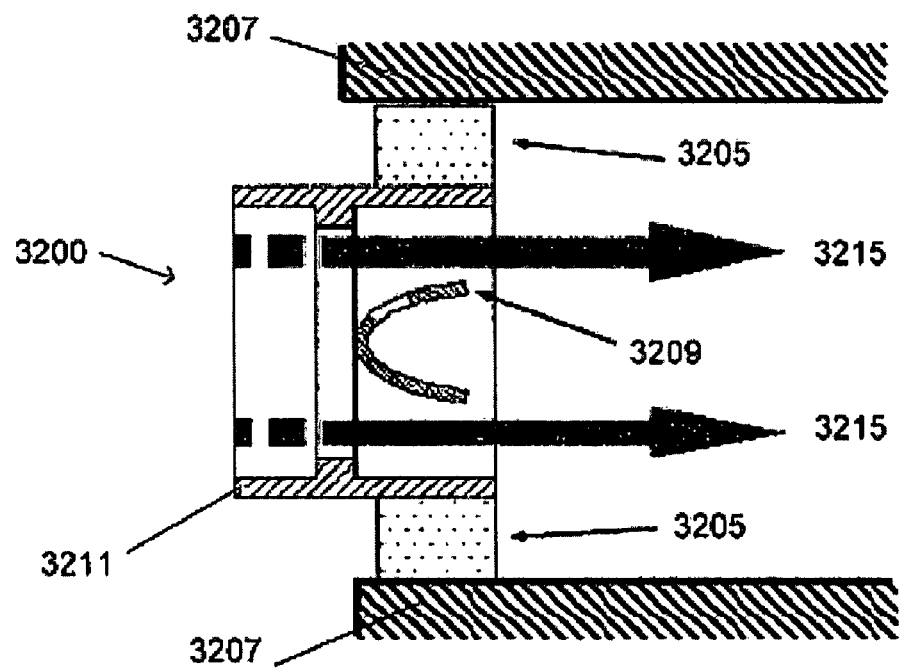
FIGS. 32a and 32b illustrate the operation of one example of a respiratory device, as described herein.
Figure 32B:
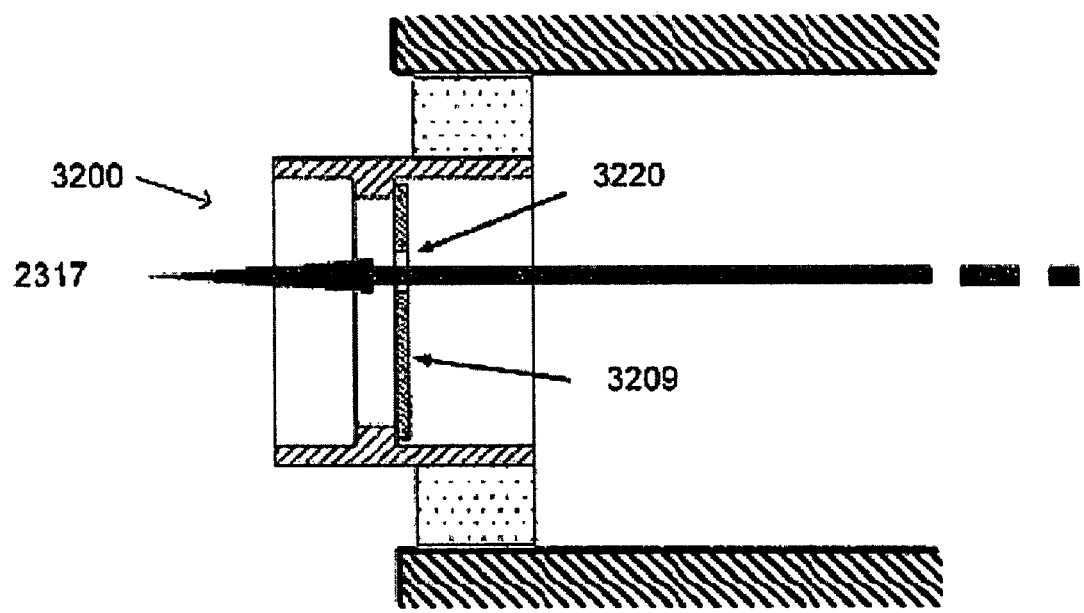

One example of a respiratory device in operation is illustrated in FIGS. 32a and 32b. The illustrated device 3200 is adapted to be removably secured in communication with a nasal cavity, and is shown inserted into a schematically-illustrated nasal cavity so that the holdfast region (shown here as foam 3205) is in communication with the nostril walls 3207. The respiratory device includes a flapper valve 3209 and a tubular body 3211. The device is oriented so that it provides a significant resistance to airflow during exhalation. FIG. 32a shows the device during inhalation, in which air is drawn into the lungs through the proximal opening in the device and out of the distal end of the tubular body. The airflow is shown by the grey arrows 3215. Pressure exerted by the subject during inhalation opens the flap valve 3209, permitting air to pass through the passageway. During exhalation, pressure pushes air from the lungs into the distal end of the device towards the proximal end, through the tubular body, causing the flap valve 3209 to close, as shown in 32b. The valve includes a leak path, holes 3220 in the valve and non-valve region (not shown). Because the combined leak path (the opening provided by the holes) is smaller than the unobstructed nasal passage, and smaller than the passage through the open device illustrated in FIG. 32a, the pressure on the distal side of the valve will be greater than it would be during the unobstructed situation, or if the valve were opened. Thus, exhalation is limited by the valve to the leak path. This may prolong expiration, and may also result in a positive end expiratory pressure (PEEP) effect.

In general, the devices described herein may create a PEEP effect by differentially changing the resistance to airflow in one direction based on the pressure applied against the device. For example, in some designs, expiratory airflow is subjected to resistance by the airflow resistor (or valve) until a certain threshold pressure differential or level of airflow is achieved; below that threshold, a more complete closure of the airflow resistor occurs (potentially completely occluding airflow through the device). The desired levels of PEEP are on the order of about 0.1 to about 30 cm $H_2O$ and more preferably about 1 to about 15 cm $H_2O$ pressure. Similarly, the differential resistance may also be triggered in the opposite direction; for example, above a certain threshold of pressure or level of airflow, the airflow resistor (e.g., valve) may open to decrease the resistance due to the airflow resistor, as when a subject coughs, sneezes, or blows his or her nose.

In some cases, the device may offer a variable resistance that is lower during the start of expiration (to promote comfort and tolerance) and that continues to increase (in a stepwise or more gradual fashion) for the remainder of expiration. In many cases, at the end of expiration, PEEP will be maintained. In still other cases, there will not be PEEP at the end of exhalation.

The use of an airflow resistor may also alter the inspiratory time:expiratory time ratio (I:E ratio), which is defined as the ratio of inspiratory time to expiratory time. The desired I:E ratio will be between about 3:1 and about 1:10 and more preferably about 1:1 to about 1:4 depending on the needs of the individual subject. In some versions, the desired ratio is approximately about 1:2.

In some versions, the device comprises an insertion, adjustment, or removal mechanism. In some cases, this mechanism involves any appropriate rigid or non-rigid positioner that facilitates removal or positioning of the device. Non-rigid positioners include but are not limited to cables, chains, wires, strings, chains, sutures, or the like. Rigid positioners include knobs, handles, projections, tabs, or the like. A user may grasp or otherwise manipulate the positioner to facilitate insertion, re-adjustment, or removal of the device. Furthermore, various applicators or other insertion devices may be used. For example, a tubular applicator holding a respiratory device adapted for insertion into a nasal cavity may be advanced into the nasal respiratory orifice (e.g., nostril) to insert the respiratory device.

In some cases, devices that insert into the respiratory orifice are oversized, or larger than the cavity (orifice) that they are to be inserted into. Oversizing the device may reduce resistance in one or more direction of airflow. In some versions, the passageway through the device is oversized. In some versions, an outer portion of the device that contacts the respiratory orifice is oversized. Thus, the respiratory device may exert pressure against the nasal cavity of a user. In subjects with obstructive sleep apnea or snoring, for example, increasing the size of a respiratory device configured to be inserted into one or more nostrils may prevent the more distal tissues of the airway, tongue, and nasopharynx from being sucked in or closed during inspiration. Moreover, airflow through an oversized passageway may assume a less turbulent flow profile, resulting in a decreased propensity for noise production in the case of snoring, for example. Similarly, the respiratory device passageway may be shaped so as to decrease turbulence of airflow. Likewise, the shape and activity of the airflow resistor may be chosen to minimize turbulence and, therefore, sound or vibration.

In some versions, devices comprise a passageway and a holdfast and may or may not include additional support such as a rim. In some cases, the holdfast may be of adequate strength to support and prevent migration or movement of the device, and to provide adequate radial support to prevent reduction of the passageway of the device during the various phases of the respiratory cycle.

In operation, the user may be asked to clean his or her nose, trim or clip his or her nose hairs, and remove all or substantially all nasal mucus or boogers. The device, especially if it is at least partially composed of foam or other deformable material, may be squeezed to reduce its size prior to insertion into the nasal cavity or nostril. In some cases, the deformable material may expand or swell over time, providing a comfortable fit and/or seal. In some cases, water or water vapor may facilitate or expedite said swelling or increase in size. In some cases, water or other liquids may fill in holes within open cell foam, therefore improving seal.

The respiratory devices may be manufactured and assembled using any appropriate method. Representative manufacturing methods that may be employed include machining, extruding, stamping, and the like. Assembling methods may include press-fitting, gluing, welding, heat-forming, and the like.

Any of the features described herein may be used with respiratory devices. Certain of the figures show features described herein, particularly FIGS. 25 through 34. FIGS. 1-24 help illustrate general principles of respiratory devices. Turning now to the figures, FIG. 1 provides a perspective view of one version of a respiratory device 1 in which the device can fit into the oral cavity of a user. The holdfast 5 comprises grooves 2 and 3 in which the user's teeth and/or gums may preferentially sit, thus securing the device in the oral cavity. Airflow resistor 4 represents any airflow resistor capable of modulating inspiratory and/or expiratory resistance during any or all portions of the respiratory cycle, as described above. The airflow resistor 4 sits within a passageway 6.

Figure 2:
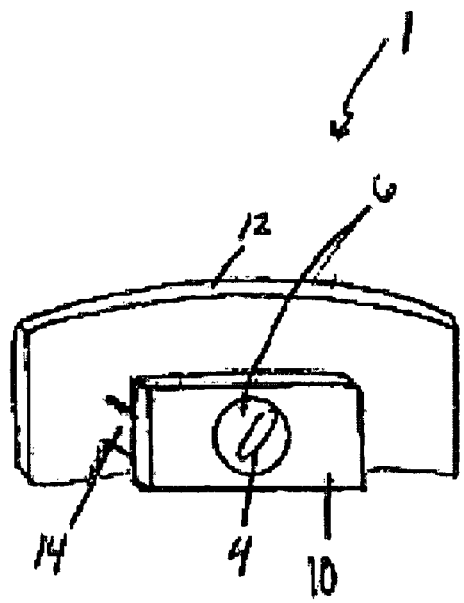
FIG. 2 is a perspective view of another respiratory device adapted for the oral cavity.

FIG. 2 is a perspective view of another embodiment of the respiratory device 1 that may be fitted in an oral cavity. In this embodiment, the subject's teeth and/or gums help to secure the device in place by contacting the holdfast. The holdfast comprises an inner frame 10, and outer frame 12, and a positioner 14. The inner frame 10 is located on the internal portions of the subject's teeth or gums. The outer frame 12 is positioned outside the subject's teeth/gums or outside the subject's lips. The positioner 14 is located between the upper and lower jaws, teeth, and/or gums. An airflow resistor 4 modulates inspiratory and/or expiratory resistance during any or all portions of the respiratory cycle.

Figure 3:
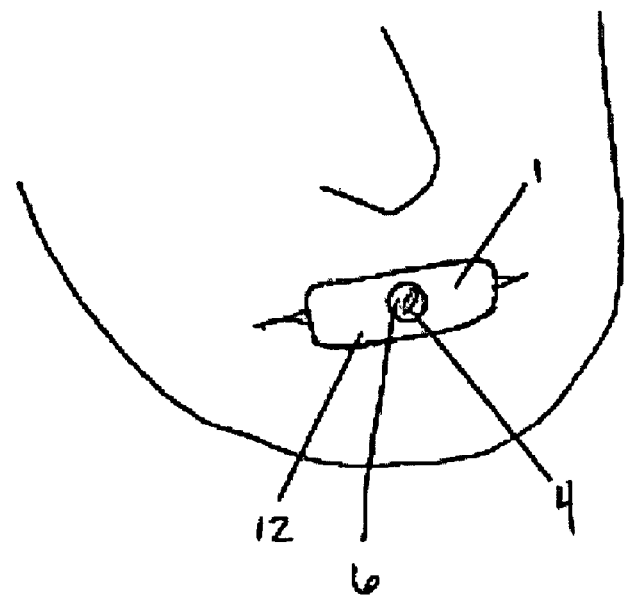
FIG. 3 is a perspective view of the device shown in FIG. 2, where the device is positioned in a subject's oral cavity.

FIG. 3 is a view of the device 1 shown in FIG. 2, where the device is depicted within and protruding from the subject's oral cavity. The outer frame 12 of the holdfast is shown outside of the subject's teeth and gums. The airflow modulator 4 within the passageway 6, modulates inspiratory and/or expiratory resistance during any or all portions of the respiratory cycle through the oral respiratory passageway. One or more airflow resistors 4 and/or passageways 6 may be used in this (or any, e.g., oral or nasal) respiratory device.

Figure 4:
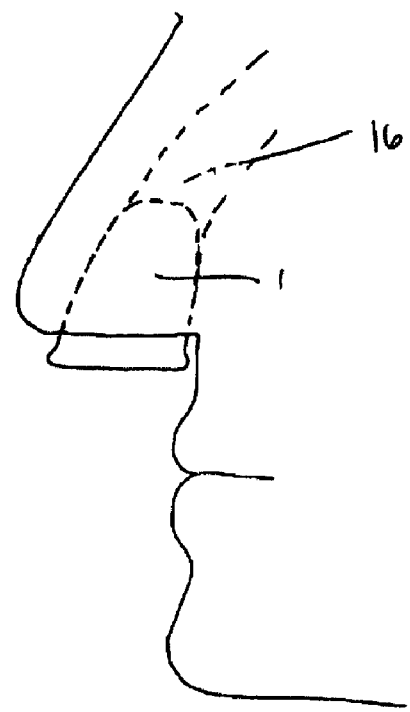
FIG. 4 shows a respiratory device adapted for the nasal cavity.

FIG. 4 is a perspective view of another embodiment of the respiratory device 1 in which the device is removable and may be secured within a subject's nasal cavity 16. In this embodiment, the device protrudes from the nasal opening. The sides of the device comprise a holdfast which is shown fitting snugly within the nasal passage, as well as projecting out from the nasal passage.

Figure 5:
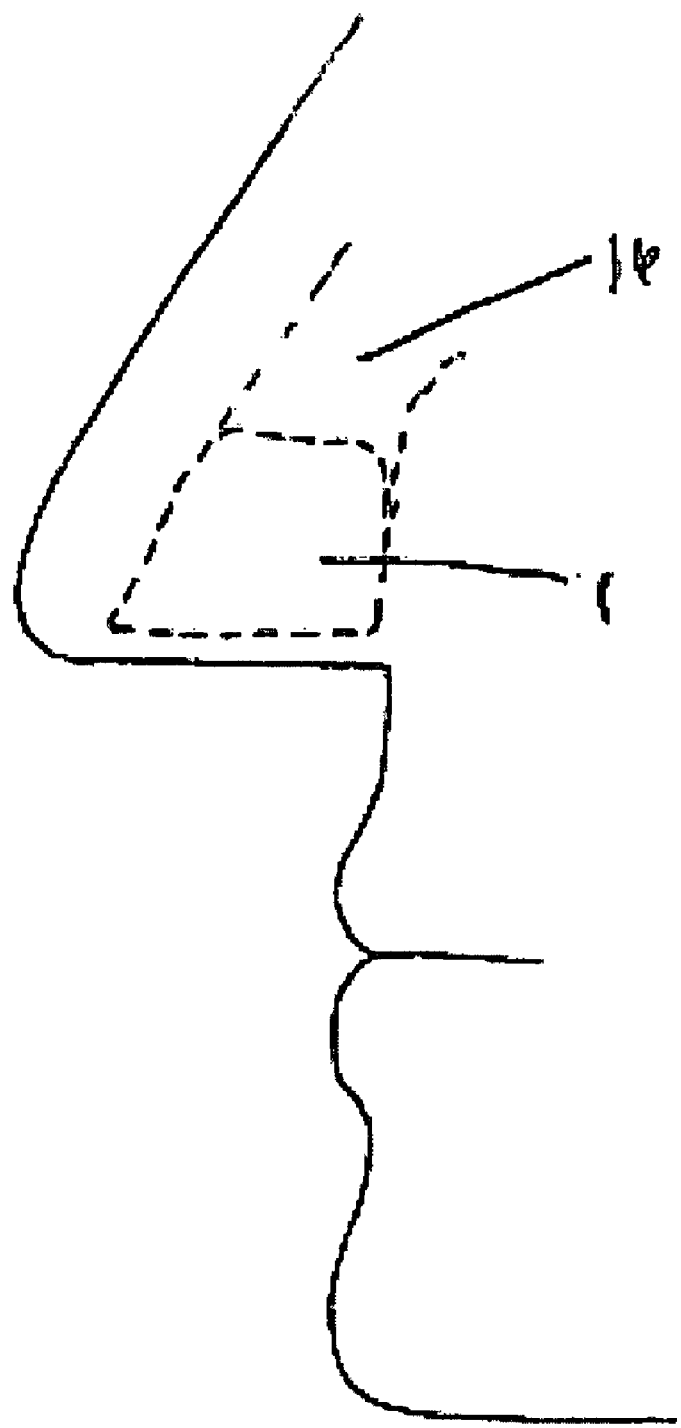
FIG. 5 shows a respiratory device adapted to fit substantially within the nasal cavity.

FIG. 5 is a perspective view of another version of the respiratory device 1 in which the device is placed completely within the nasal passage 16. The entire respiratory device fits snugly within the nasal passage.

Figure 6:
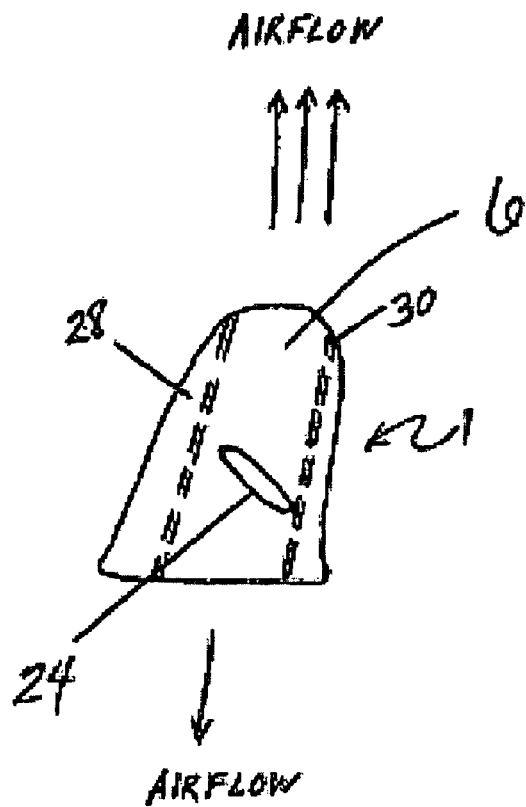
FIG. 6 shows a cross-sectional view of the device shown in FIG. 4, where an airflow resistor is shown within the device.

FIG. 6 is a cross-sectional view of a respiratory device 1 similar to those shown in FIGS. 4 and 5. A holdfast 28 comprises the outer surface of the device that contacts the inner portions of the nasal cavity, thus serving to secure the device in place while ideally creating a partial or complete seal. The passageway 6 through which air may flow is surrounded by a rim 30 that provides additional structural support to the device. A rim 30 is not required, particularly if the walls of the passageway (which may be defined by the holdfast 28, for example) provide sufficient support. An airflow resistor 24 is included within the passageway which may modify inspiratory and/or expiratory resistance during any or all portions of the respiratory cycle.

Figure 7A:
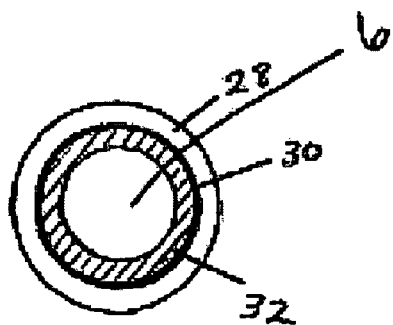
FIGS. 7a and 7b show cross-sectional views of the device shown in FIG. 4.
Figure 7B:
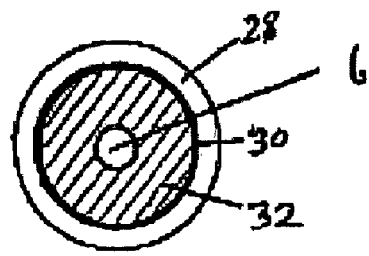

FIGS. 7a and 7b show more detailed views of the operation of airflow resistors shown in FIGS. 4 and 5. These cross-sectional views illustrate the holdfast 28, the optional rim 30, the passageway 6, and the airflow resistor, shown as a valve 32. The rim 30 separates the holdfast 28 and the valve 32, frames the valve 32, and provides overall structural support to the entire device. In FIG. 7a, the valve 32 is shown in the open position, providing less resistance to airflow. In FIG. 7b, valve 32 is shown in the closed position, providing more resistance to airflow, because the cross-sectional area of the passageway 6 has been constricted by the closing of the valve.

Figure 8A:
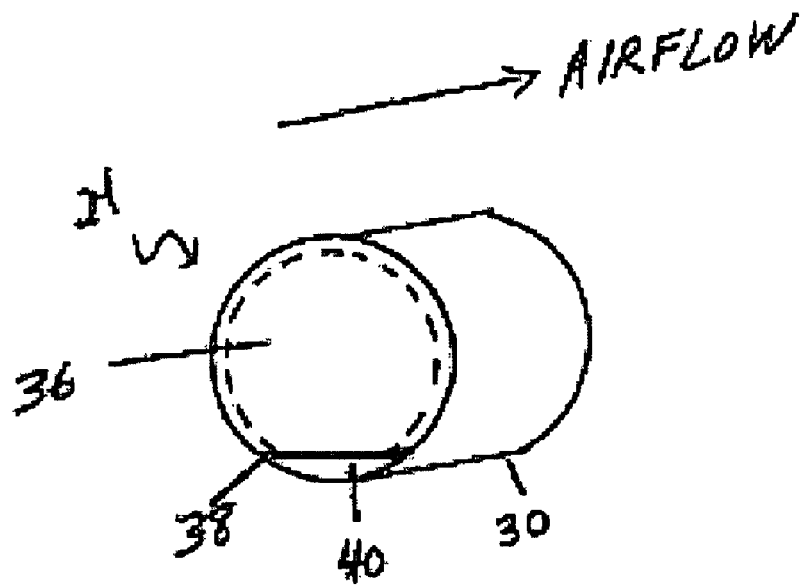
FIGS. 8a and 8b are perspective views of a respiratory device showing an airflow resistor during exhalation (FIG. 8a) and inhalation (FIG. 8b), respectively.
Figure 8B:
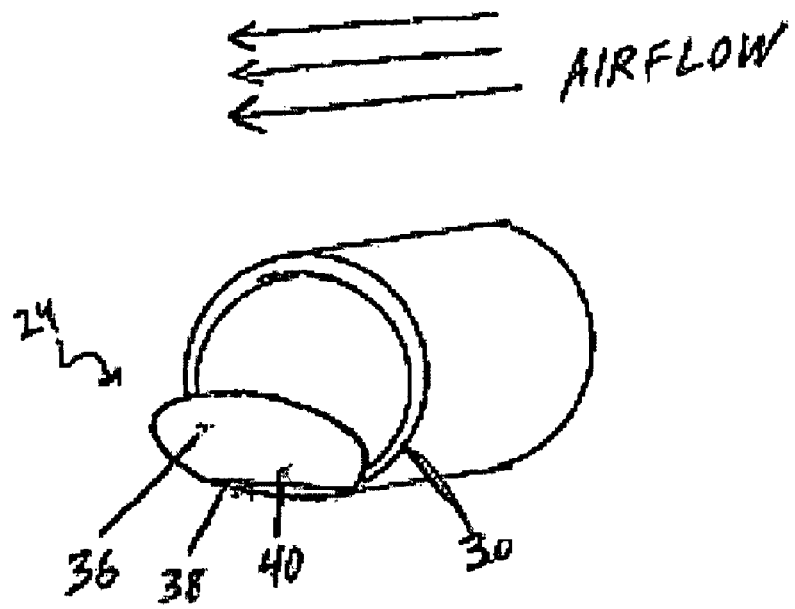

FIGS. 8a and 8b show perspective views of an airflow resistor that could be used, for example with any of the devices described in FIGS. 1-5. In these figures, a rim 30 is shown. The rim may be part of the holdfast which positions and secures the device within a respiratory passageway; alternatively, additional material (e.g., compliant material) may be attached to the rim to form the holdfast. In FIGS. 8a and 8b, the rim provides support to the airflow resistor 24. The airflow resistor is shown here as a flap valve mechanism that comprises a flap 36 that pivots around a joint 38 and is connected to a fixed element 40. Fixed element 40 is attached to the inner region of the passageway 6, which is defined in this figure by the rim 30. In some versions, the flap valve and the inner surface of the passageway 6 (e.g., the rim 30) may constitute a single piece. Alternatively, the flap 36, joint 38, and fixed element 40 may be fabricated as a single piece, in which case joint 38 may be a hinge. Thus, joint 38 may be a pinned hinge or a non-pinned hinge joint. Alternatively, rim 30, flap 36, joint 38, and fixed element 40 may all be created as a single piece or material. Thus, flap 36 is able to pivot in relation to fixed element 40 depending on the direction of the subject's airflow and the desired level of resistance to airflow. FIG. 8a shows the airflow resistor with flap 36 in a closed position during expiration, thus providing increased resistance. In some versions, the flap portion of the airflow resistor closes completely, as shown. In these versions, the edges of the flap 36 may close off the entire passageway (as shown), or may only occlude a portion of the passageway. FIG. 8b shows the airflow resistor with flap 36 in the open position (e.g., during inspiration), thus providing decreased resistance. Flap 36 may define a hole, or may have other openings (which may stay open during all or part of the respiratory cycle) to help modulate the degree of inspiratory and expiratory resistance. The flap 36 may return to a preferred opened or closed position. For example, a bias such as a shape memory material, a spring (such as a torsion spring), or the holdfast may apply force to flap 36 to return it to a closed position. For example, the use of foam or urethane surrounding the airflow resistor may provide such force as to close flap 36 in the absence of adequate airflow. Bi-leaflet versions of the airflow resistor are also contemplated and will have similar function. These bi-leaflet versions may involve multiple sets of flaps 36, joints 38, and fixed elements 40, etc.

Figure 9A:
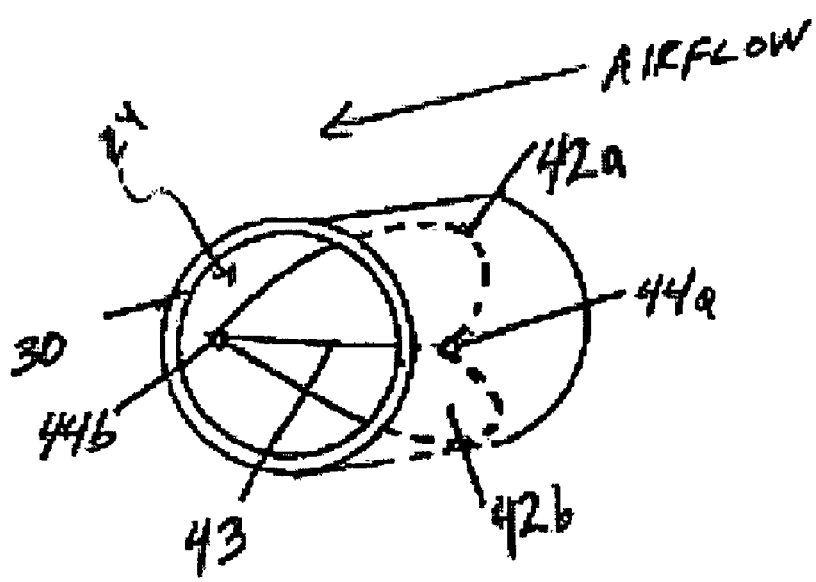
FIGS. 9a and 9b are perspective views of a respiratory device having an airflow resistor where the airflow resistor is shown during exhalation (FIG. 9a) and inhalation (FIG. 9b), respectively.
Figure 9B:
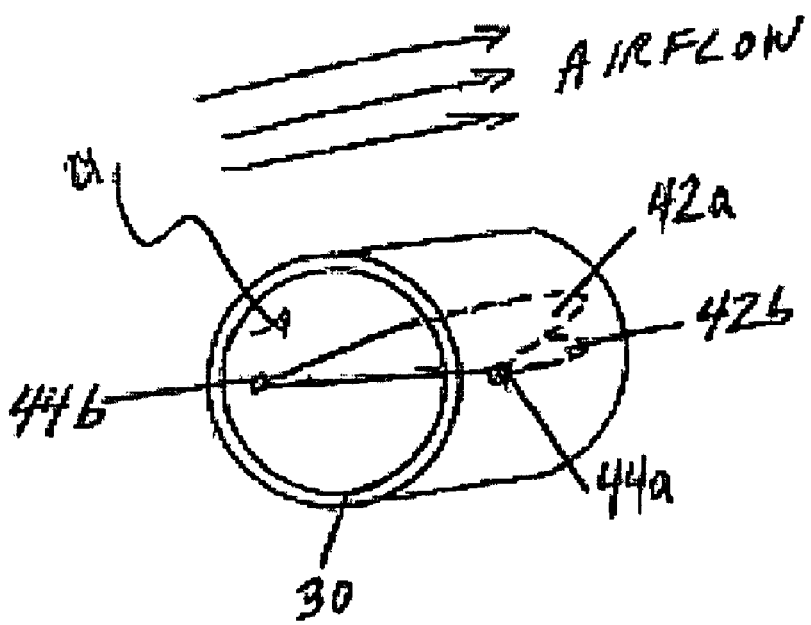

FIGS. 9a and 9b show a perspective view of another embodiment of an airflow resistor that could be used in any of the respiratory devices described herein. The inner surface of the passageway shown includes a rim 30 that supports the airflow resistor. This airflow resistor 24 is also shown as a valve mechanism. Moveable elements 42a and/or 42b (flaps) are attached to one another or are constructed from a single piece. Moveable elements 42a and 42b are attached to the inner surface of the passageway (shown as a rim 30) at attachment points 44a and 44b, and these attachment points may allow the valve to pivot around a hinge 43 in response to direction and amplitude of airflow. In one version, attachment points 44a and 44b are formed directly into the rim 30 or holdfast 28 during the manufacturing (e.g., casting) process. In one version, the hinge is statically attached to an inner region of the passageway, and the flaps 42a and 42b are movably (or flexibly) attached to the hinge. FIG. 9a shows this airflow resistor when the resistance is high (e.g., the flap valve is mostly closed), as during expiration, and FIG. 9b shows the airflow resistor when the resistance is low (e.g., the flap valve is mostly open), as during inspiration.

Figure 10:
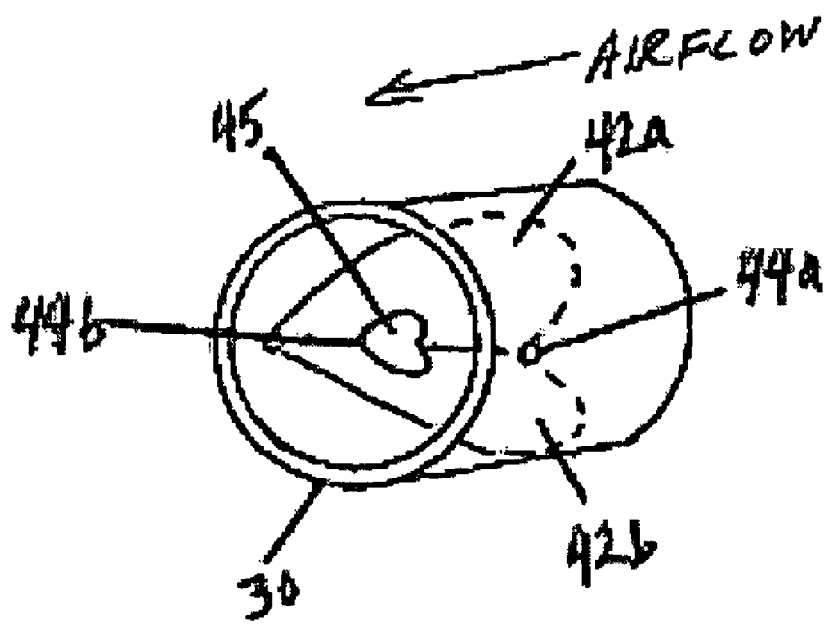
FIG. 10 is a perspective view of a respiratory device having an airflow resistor where the airflow resistor is shown during exhalation.

FIG. 10 shows a perspective view of another embodiment of an airflow resistor that is similar in structure and function to the device shown in FIGS. 9a and 9b. However, the airflow resistor shown has an internal opening 45 that is located approximately where moveable elements 42a and 42b pivot relative to one another. The addition of internal opening 45 modulates airflow (e.g., inspiratory or expiratory airflow) by altering the level of resistance. Addition of this opening reduces the resistance in one direction (e.g., expiratory resistance, when the flap valve is "closed") more than resistance in the opposite direction (e.g., inspiratory resistance, when the flap valve is "open").

Figure 11:
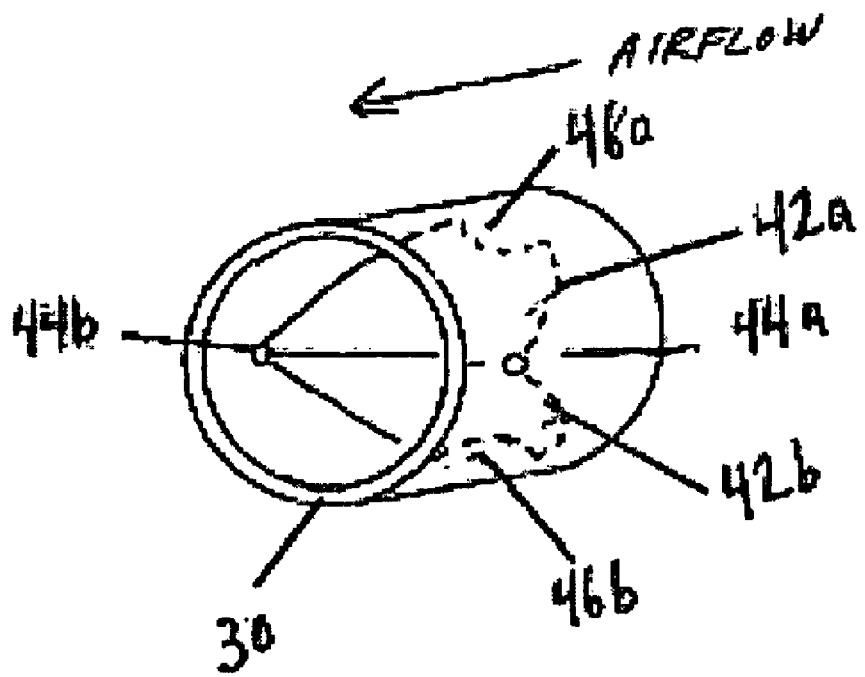
FIG. 11 is a perspective view of a respiratory device having an airflow resistor where the airflow resistor is shown during exhalation.

FIG. 11 shows a perspective view of another embodiment of an airflow resistor that is similar in structure and function to the device shown in FIGS. 9a and 9b. Peripheral openings 46a and 46b are placed completely within, or on the periphery of the moveable elements 42a and 42b. These peripheral openings 46a and 46b also modulate inspiratory and/or expiratory resistance. The addition of peripheral openings 46a and 46b helps modulate inspiratory and expiratory airflow by altering the level of resistance. Addition of these peripheral openings also reduce the resistance in one direction (e.g., expiratory resistance, when the flap valve is "closed") more than resistance in the opposite direction (e.g., inspiratory resistance, when the flap valve is "open").

Figure 12A:
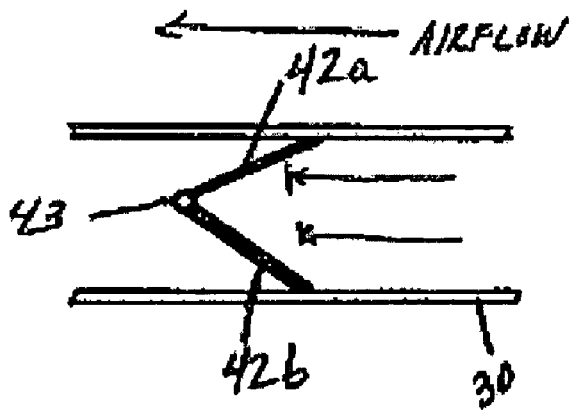
FIGS. 12a and 12b show cross-sectional views of the respiratory devices shown in FIGS. 9a, 9b, 10, and 11 during exhalation (FIG. 12a) and inhalation (FIG. 12b), respectively.
Figure 12B:
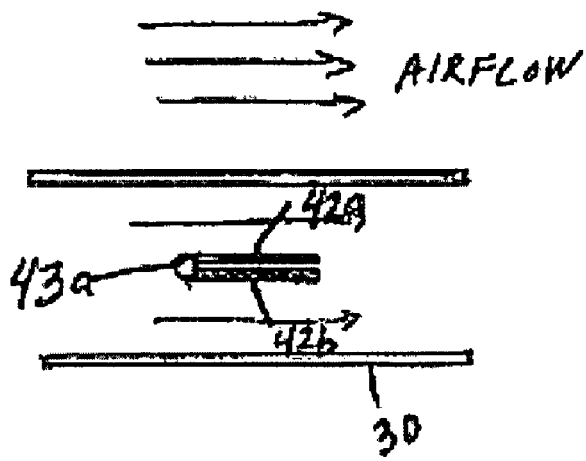
Figure 12C:
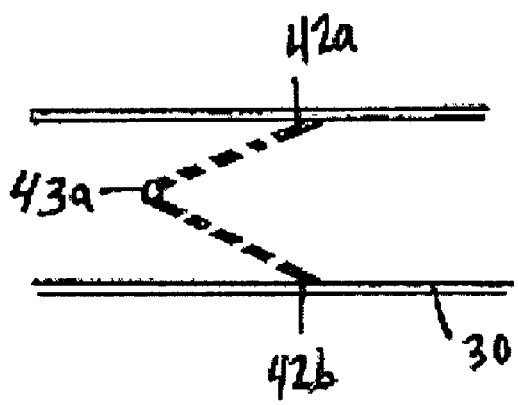
FIG. 12c shows a cross-sectional view of a variation of the respiratory device during exhalation.

FIGS. 12a and 12b show more detailed views of the operation of the valve mechanisms as described in FIGS. 9a, 9b, 10, and 11. In this figure, we assume that the airflow resistor is oriented so that the airflow resistor increases resistance during expiration relative to inhalation (e.g., the lungs are located to the right in FIGS. 12a, 12b and 12c). Moveable elements 42a and 42b are coupled to each other via hinge 43. FIG. 12a demonstrates the valve mechanism during expiration, in which moveable elements 42a and 42b are in a closed position due to the expiratory airflow in the direction from the lungs to the external environment. FIG. 12b demonstrates the valve mechanism during inspiration, in which moveable elements 42a and 42b are in an open position due to the inspiratory airflow in the direction from the external environment to the lungs. FIG. 12c demonstrates a modification of the valve mechanism shown in FIGS. 12a and 12b in which there are one or more apertures within or on the periphery of the moveable elements that reduce resistance to expiratory airflow, further increasing the rate of expiratory airflow. All of these valve mechanisms and configurations can be placed in the opposite orientation so that inspiratory airflow leads to valve closure and expiration leads to valve opening.

Moveable elements (flaps) 42a and 42b of the airflow resistor may be made of any appropriate material. In particular, materials which have sufficient stiffness to withstand the forces applied by the respiratory process. Furthermore, durable materials (e.g., which may withstand the moisture, etc. of the respiratory passage) may also be desirable. In some versions, the devices are disposable, and thus durability may be less critical. Furthermore, the moveable elements 42a and 42b may also be made from porous materials or filters, etc. that do not overly restrict or resist airflow but at the same time can remove debris, pollen, allergens, and infectious agents for example.

Figure 13A:
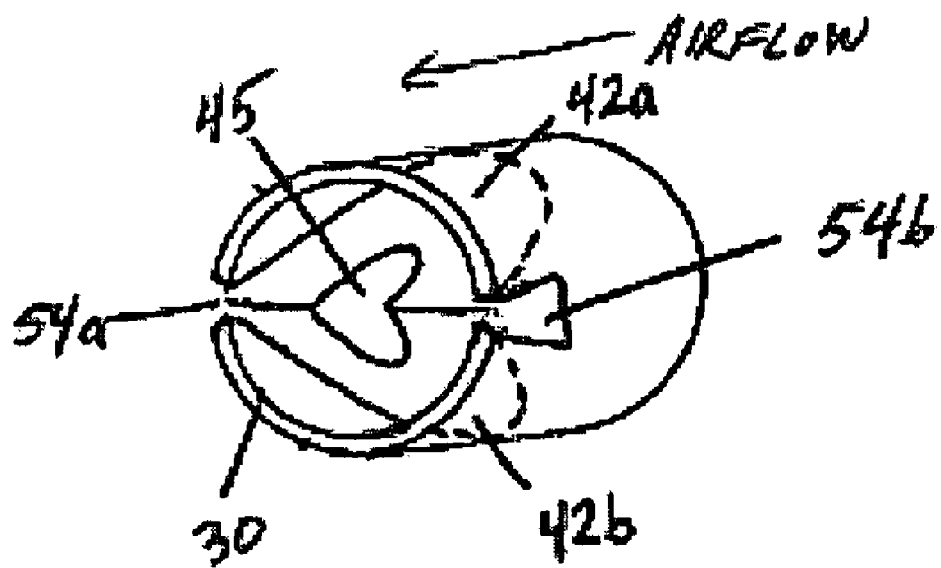
FIGS. 13a and 13b are perspective views of a respiratory device having an airflow where the airflow resistor is shown during exhalation (FIG. 13a) and inhalation (FIG. 13b), respectively.
Figure 13B:
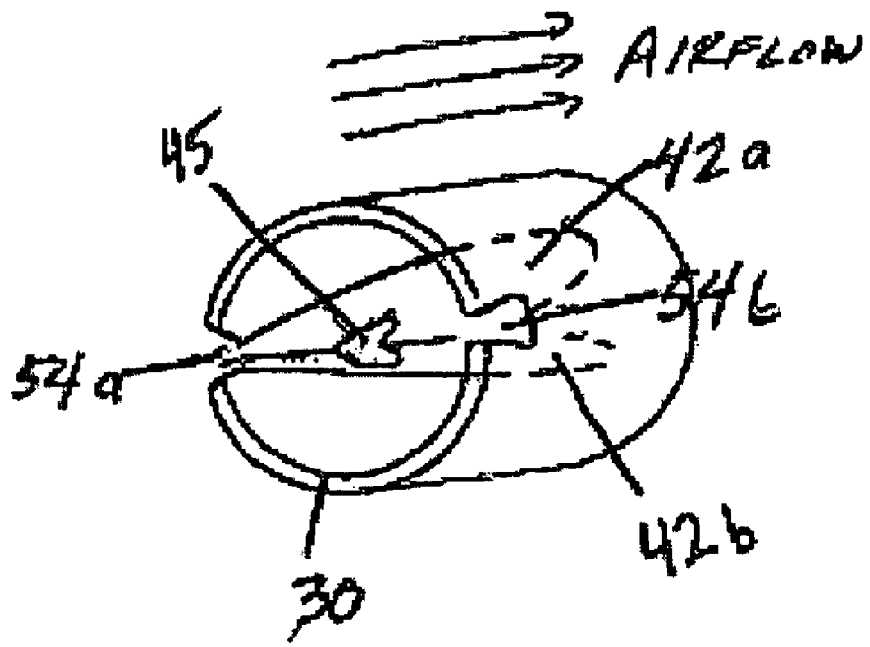

FIGS. 13a and 13b show perspective views of another airflow resistor that could be used in any of the devices described herein. FIG. 13a shows the airflow resistor (a flap valve) in a closed position, as might be seen during expiration, resulting in increased resistance to airflow. FIG. 13b shows the airflow resistor in an open position, as might be seen during inspiration, resulting in a decreased resistance to airflow relative to the closed position. Because of the small profile of the retracted flap valves, the resistance added by the airflow resistor when the airflow resistor is "open" may be negligible. Moveable elements 42a and 42b are attached to each other or are a single piece. Moveable elements 42a and 42b are attached to the walls of the passageway (in this example, defined by a rim 30), to the rim 30, or to the holdfast 28 by a securing element 54a and 54b which uses a tab, adhesives, press fit, external pressure (as from a holdfast 28) or any way known to those skilled in the art. Internal opening 45 is located centrally, decreasing the resistance to expiratory airflow (in the "closed" state), although peripheral locations are also contemplated. In some versions, the size and number of openings (e.g., the leak paths) in the valves may determine the resistance of the airflow resistor during expiration and inspiration.

Figure 14:
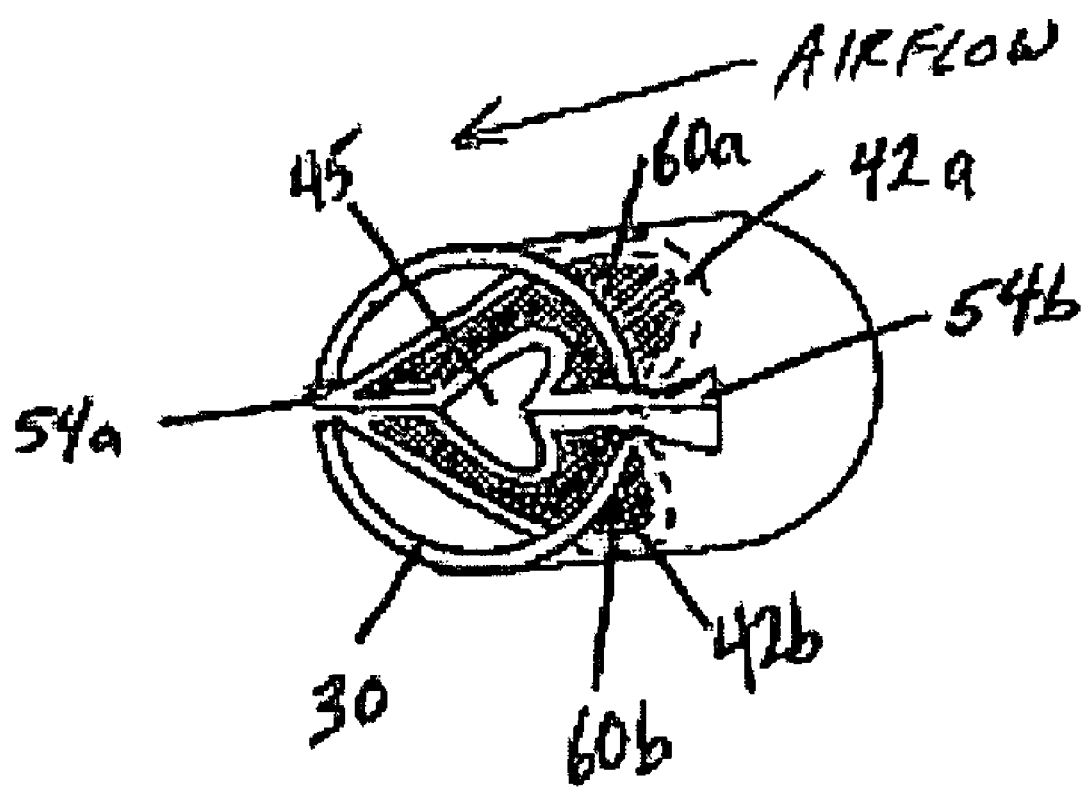
FIG. 14 is a perspective view of a respiratory device having an airflow resistor where the airflow resistor is shown during exhalation.

FIG. 14 provides a perspective view of another embodiment of an airflow resistor that is similar in structure and function to the airflow resistor shown in FIGS. 13a and b. In FIG. 14, the movable elements further comprise a flap reinforcement 60a and 60b that is located partially or completely covering the moveable elements 42a and 42b. The flap reinforcement provides additional structure and/or stiffness to these moveable elements. Furthermore, flap reinforcement 60a and 60b may also promote a more reliable seal and may standardize the movements of moveable elements 42a and 42b while reducing the likelihood that moveable elements will invert, buckle in the direction of airflow, or otherwise fail, especially when exposed to high pressures and airflow as might be seen during coughing, although an additional flap valve support (not shown) may also be used. The addition of flap reinforcements 60a and 60b also dampens any whistling or other sounds during inspiration or expiration. Moveable element 42a and flap reinforcement 60a and moveable element 42b and flap reinforcement 60b may be a single unit (or each "flap" may be a single unit). Alternatively, both moveable elements 42a and 42b and both flap reinforcements 60a and 60b may be a single unit. A central leak path opening 45 is also shown in the figure.

Figure 15A:
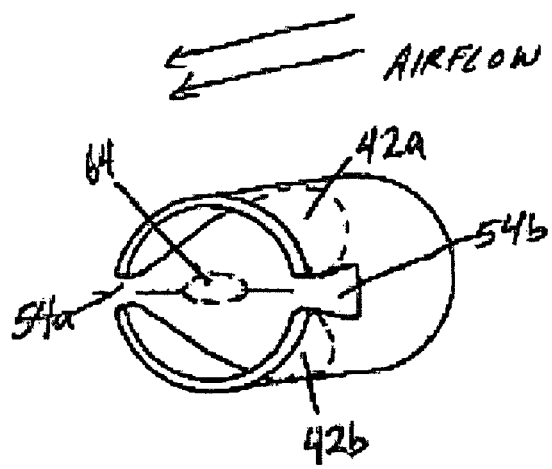
FIGS. 15a, 15b, and 15c are perspective views of a respiratory device having an airflow
Figure 15B:
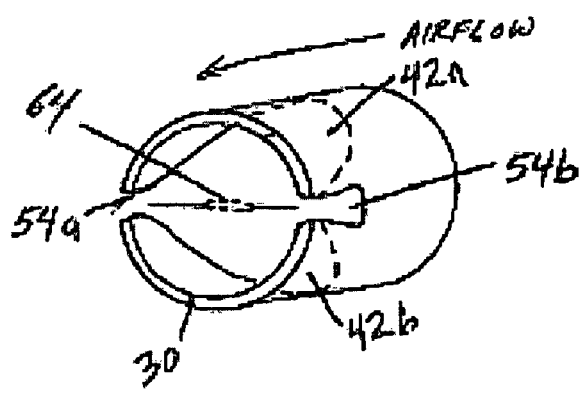
Figure 15C:
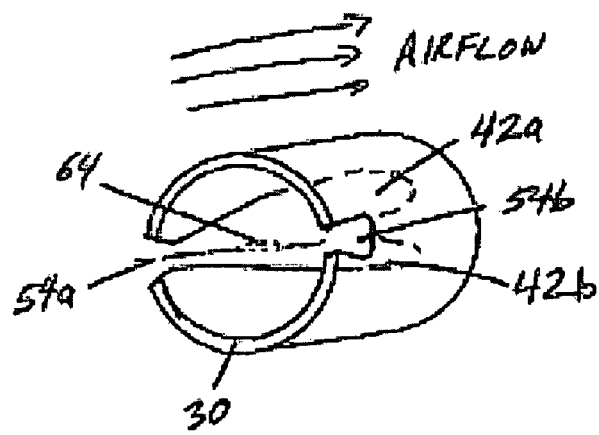

FIGS. 15a-15c show perspective views of another embodiment of an airflow resistor that may be used in any of the devices described herein. The airflow resistor is similar to that shown in FIGS. 13a and 13b with the exception that internal opening 45 is replaced by another airflow resistor 64 (a "nested airflow resistor"). This nested airflow resistor 64 automatically closes when the flow through the valve (or the pressure differential across the valve) falls below a predetermined level. This allows the airflow resistor (with the nested airflow resistor region) to provide positive end expiratory pressure (PEEP). In FIG. 15a, the airflow resistor is shown during exhalation, and the moveable elements 42a and 42b of the airflow resistor are in the closed position. The nested portion of the airflow resistor 64 is open so long as the pressure differential across the airflow resistor and/or airflow is above a certain level. Thus, this figure demonstrates the beginning of expiration, when airflow in the passageway and pressure differential are largest. In FIG. 15b, the same airflow resistor is again shown during expiration, and moveable elements 42a and 42b of the airflow resistor are still in the closed position. However, the nested airflow resistor region 64 now assumes a closed position, since the pressure differential across the airflow resistor and airflow through the passageway is no longer above the threshold value. This scenario may correspond to the later stages of exhalation, when airflow and pressure differential are decreasing or are lower. Thus, at the end of exhalation, PEEP has been created. For example, the nested airflow resistor 64 may be set to close whenever air pressure in the respiratory orifice coming from the lungs is less than 10 cm $H_2O$, or less than 5.0 cm $H_2O$, or any value from 1 to 25 cm $H_2O$. FIG. 15c shows the device during inhalation, in which moveable elements 42a and 42b of the airflow resistor are in the open positions, allowing inhalatory airflow with minimal resistance to said airflow.

Figure 16:
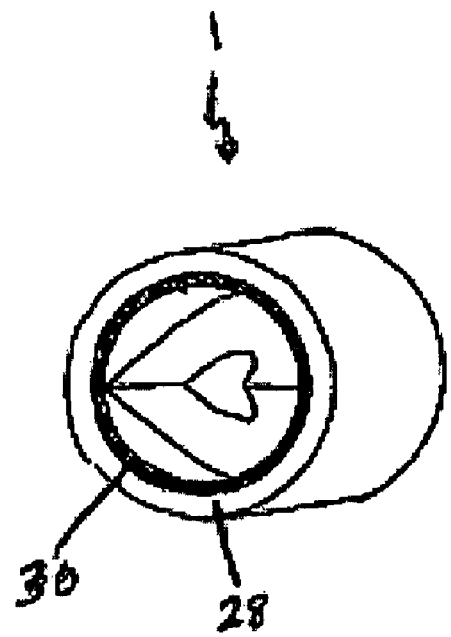
FIG. 16 is a perspective view of a respiratory device where the device is removable and for the nasal cavity.

FIG. 16 is a perspective view of another embodiment of the respiratory device where the device is removable and may be placed in communication with the nasal cavity. In FIG. 16, a holdfast 28 is located between the subject's nose and the airflow resistor in the device 1, providing a partial or complete seal, anchoring the device, and providing comfort for the subject. The holdfast 28 has a cross section that is roughly circular and capable of fitting within a subject's nostrils.

Figure 17:
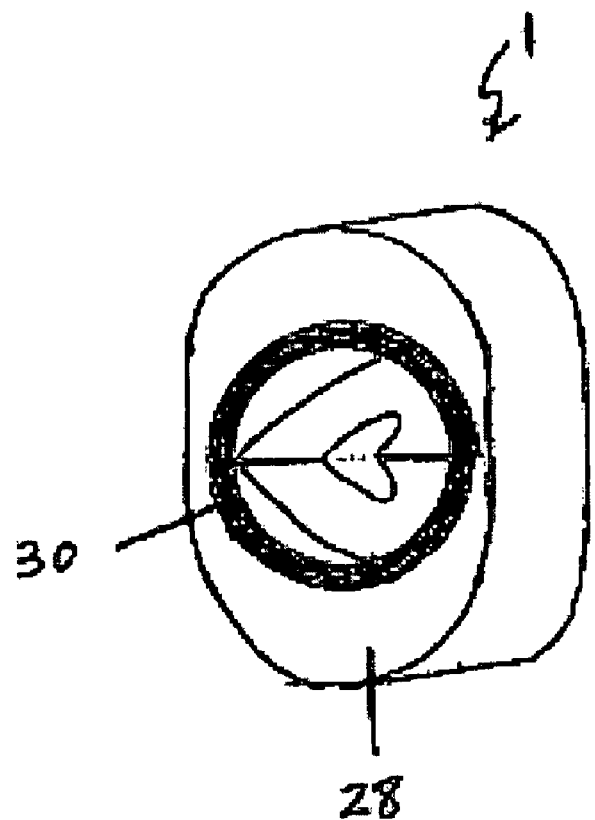
FIG. 17 is a perspective view of a respiratory device where the device is removable and for the nasal cavity.

FIG. 17 is a perspective view of another embodiment of a respiratory device where the device is removable and may be placed within the nasal opening. This device shows a holdfast 28 having an approximately oval cross-section. Many such cross-sectional shapes are possible to optimize placement, anchoring, sealing, and comfort, including a variety of conical or asymmetric shapes designed to fit within a subject's nasal openings. In some cases, the rim 30 and/or any airflow resistor 4 may also assume any desired cross sectional shape, including that of an oval or any other non-circular orientation. In some embodiments, the holdfast 28 will be shapeable, deformable, or adjustable by the subject either before, after, or during placement of the device. Alternatively, the device can be customizable to fit individual subjects through the use of imaging modalities including MRI, CT, x-ray, or direct vision, or through the use of molding techniques that are common in dentistry and other fields.

Figure 18:
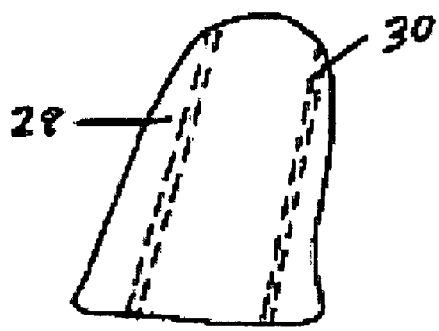
FIG. 18 is a cross-sectional view of a respiratory device where the device is removable ted for the nasal cavity.

FIG. 18 is a cross-sectional view of an embodiment of a respiratory device where the device is removable and may be secured in fluid communication with a nasal cavity. The device comprises a holdfast 28 and rim 30 that lends the device support. The device may be oversized to decrease resistance and increase airflow in one or more directions. In some cases, a drug (with either an active or inactive ingredient) may be embedded in or located on any of the device's components, for example, the rim 30. It is appreciated that in some cases, there may be no rim 30, so long as structural support is provided by another component of the device, e.g., the holdfast. In this case, the drug may be loaded or coated on the holdfast or within the passageway.

Figure 19:
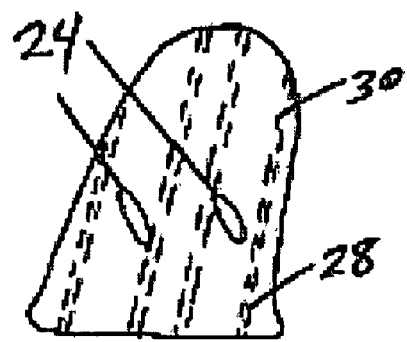
FIG. 19 is a cross-sectional view of a respiratory device where the device is removable ted for the nasal cavity.

FIG. 19 shows a cross-sectional view of another embodiment of a respiratory device where the device is removable and may be secured in communication with a nasal cavity. In this figure, there are two airflow passageways. Each passageway is shown with an airflow resistor 24 therein. The holdfast 28 surrounds both passageways, and each passageway includes an (optional) rim 30. Each of the flow resistors 24 may increase or decrease resistance to airflow independently and may work simultaneously or at different times during the respiratory cycle. For example, in some cases, during inhalation, one of the airflow resistors 24 may decrease resistance to airflow while the second airflow resistor 24 increases resistance to airflow. On exhalation, the first airflow resistor 24 may increase resistance to airflow while the second airflow resistor 24 decreases resistance to airflow. In other words, inspiratory airflow may proceed through one location, and expiratory airflow may proceed through a second location within the same device.

Figure 20:
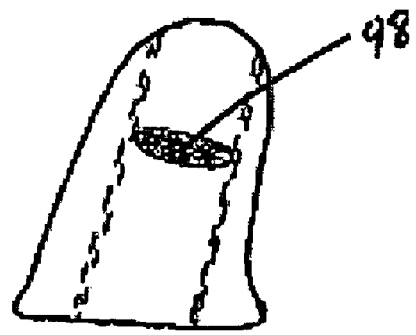
FIG. 20 is a cross-sectional view of a respiratory device where the device is removable ted for the nasal cavity.

FIG. 20 is a cross-sectional view of another embodiment of the respiratory device where the device is removable and may be secured in communication with a nasal cavity. The device is shown with a fixed filter 98 that is located in the path of the airflow as it traverses the device. The fixed filter 98 may help clear the airflow of any solid or liquid particles, debris, odors, allergens, pollen, and/or infectious agents. This filter 98 may remain roughly fixed in place during all parts of the respiratory cycle though some degree of movement may be permitted. A drug may be placed within or on the surface of one or more components of the device to provide additional benefit to the subject. The addition of fixed filter 98 may not lead to increased resistance in either direction, unless such a design is desired. The fixed filter 98 can be created from any number of filter materials that are known to those skilled in the art. This fixed filter 98 may be used in any of the respiratory devices herein, in addition to, or as an alternative to, an airflow resistor 4.

Figure 21:
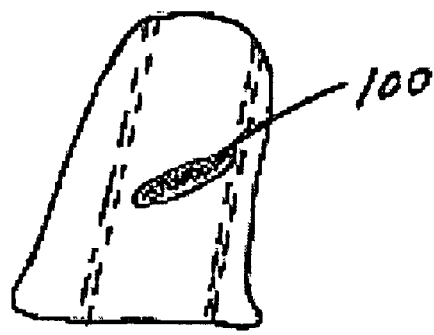
FIG. 21 is a cross-sectional view of a respiratory device where the device is removable ted for the nasal cavity.

FIG. 21 is a cross-sectional view of another embodiment of the respiratory device, where the device is removable and may be secured in communication with a nasal cavity. The respiratory device of FIG. 21 comprises a moveable cleansing filter 100 that is shown located within the device, and which may help to clear the airflow of solid or liquid particles, debris, odors, allergens, pollen, and/or infectious agents. In some versions, the filter may be configured to move so that it filters only during inhalation (or exhalation), or may move out of the way during periods of extremely large airflow (or air pressure) in the airflow passageway (e.g., during coughing, nose blowing, sneezing).

Figure 22A:
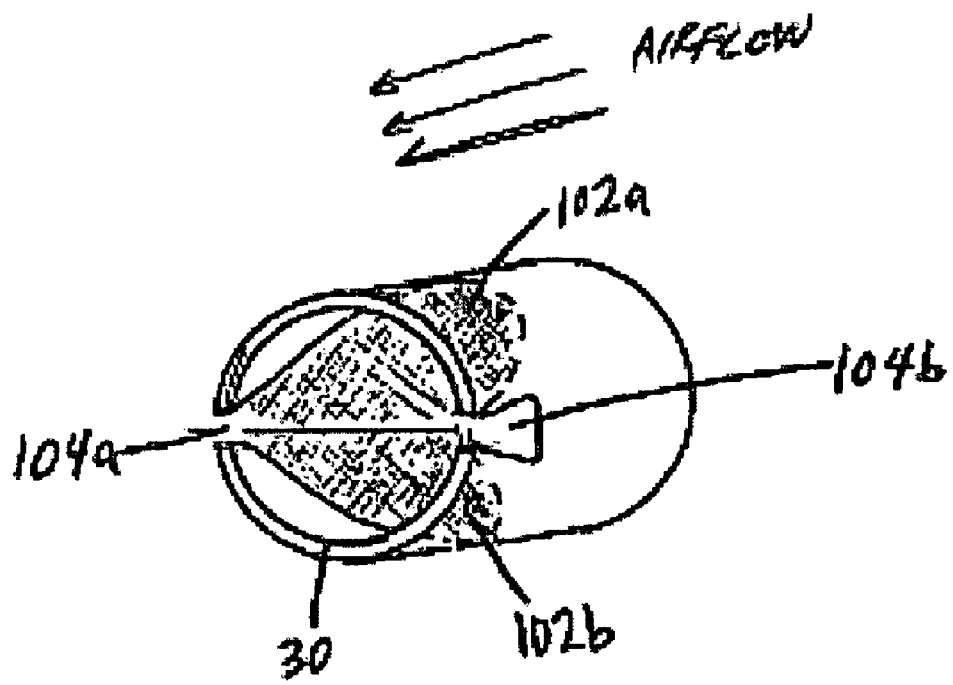
FIGS. 22a and 22b are perspective views of a respiratory device having a moveable air filter where the moveable air filter is shown during inhalation (FIG. 22a) and exhalation (FIG. 22b), respectively.
Figure 22B:
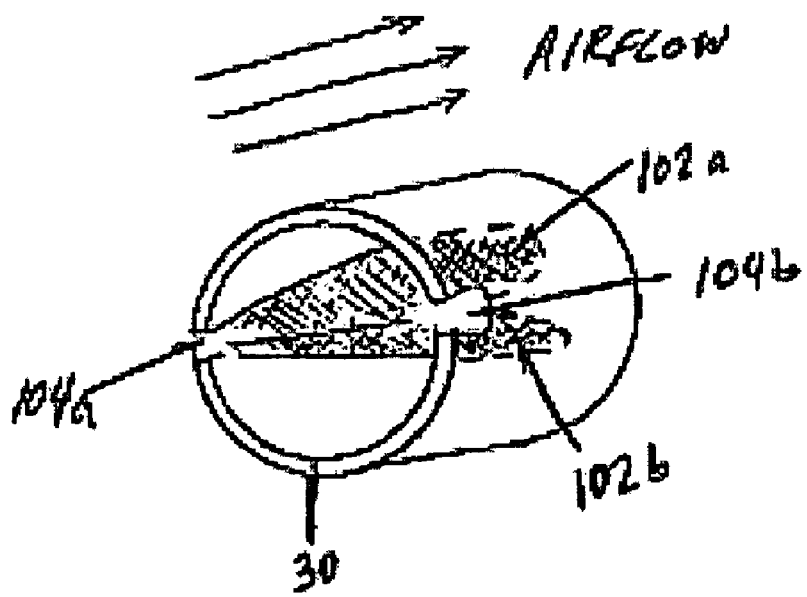

FIG. 22a and 22b are perspective views of one version of a moveable cleansing filter where the moveable cleansing filter is shown during inhalation and exhalation respectively. A movable cleansing filter may be a movable filter, scrubber, or any other device capable of removing (particularly selectively removing) any solid or liquid particles, debris, odors, allergens, pollen, and/or infectious agents. This moveable cleansing filter may be used in any of the respiratory devices herein, in addition to, or as an alternative to, an airflow resistor 4. FIG. 22a shows the moveable cleansing filter (shown as movable filters) during inspiration (during which airflow travels from right to left in the figure) leading to displacement of moveable filter elements 102a and 102b away from one another. FIG. 22b shows the moveable cleansing filter during expiration (during which airflow travels from left to right in the figure) leading to displacement of moveable filter elements 102a and 102b towards one another. Thus, on inspiration, airflow passes through the moveable filter elements 102a and 102b and the air may be cleansed of the relevant substances. On expiration, airflow passes both through and around moveable filter elements 102a and 102b. The addition of moveable filter elements 102a and 102b ideally does not lead to increased resistance in either direction, unless such a design is desired. The moveable filter elements 102a and 102b can be created from any number of filter materials that are known to those skilled in the art. One or more openings or apertures may be placed within the moveable filter elements 102*a* and 102*b* to alter inspiratory or expiratory resistances.

Figure 23:
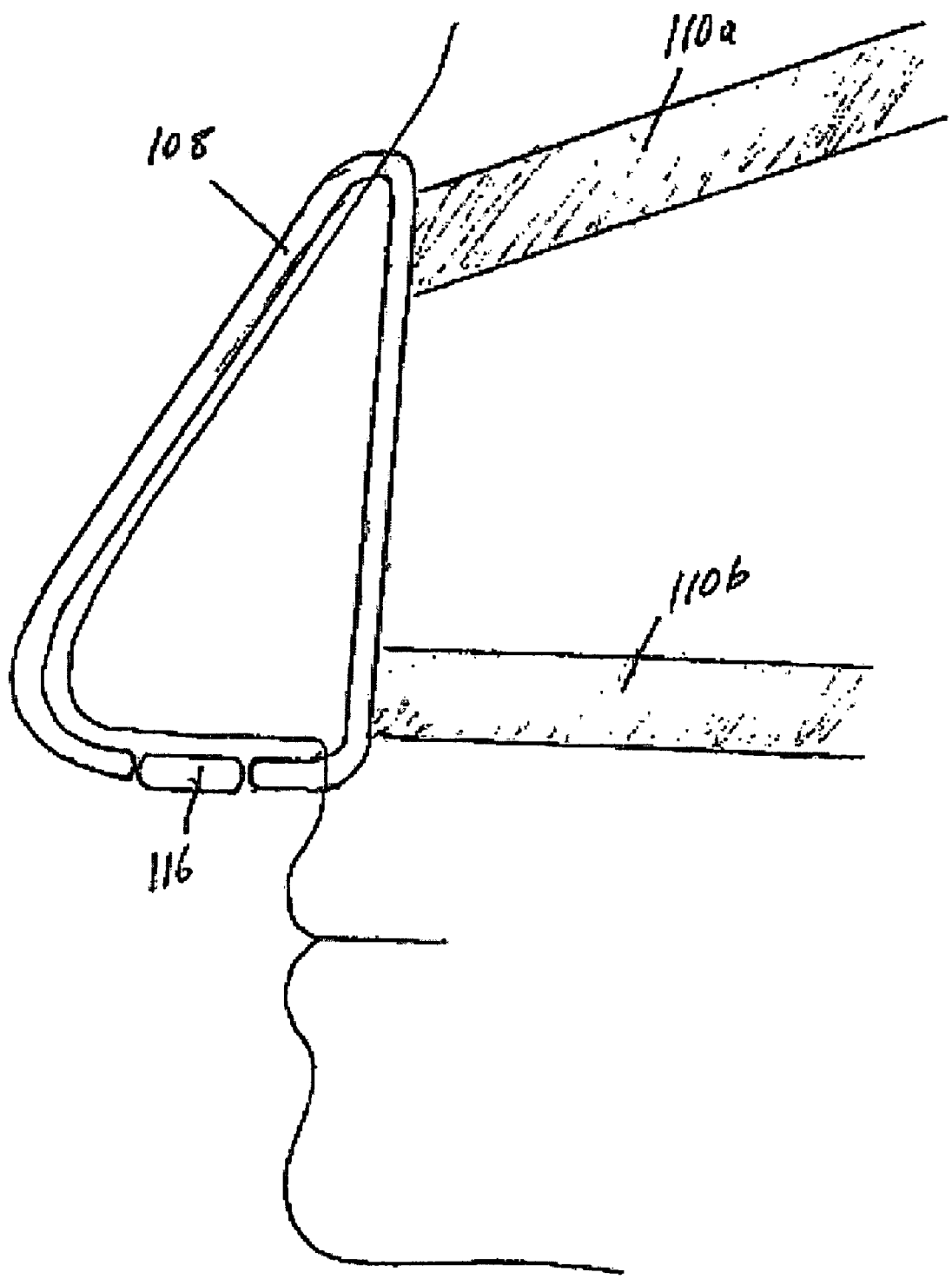
FIG. 23 is a perspective view of another respiratory device where the device is removable and adapted for the nasal cavity.

FIG. 23 is a perspective view of another embodiment of the subject devices where the device is removable and secured in communication with both nasal cavities. Nasal mask 108 is positioned securely against the nose and face in order to minimize or eliminate the possibility of air leak around the periphery of the device. The device includes a holdfast comprising straps 110*a* and 110*b* (that facilitate the secure positioning) and a nasal mask 108 that is secured against the face by the straps. The mask's airflow resistor 116 modulates inspiratory and/or expiratory resistance during any or all portions of the respiratory cycle. There is at least one airflow resistor 116 located on the device, though two or more airflow resistors 116 may be used (e.g., one placed in proximity to each nostril). An adhesive may find use with this embodiment, to help promote a seal or anchoring of the device.

FIG. 24 is a cross-sectional view of another embodiment of a respiratory device, where the device is removable and may be secured in communication with a nasal cavity. In FIG. 24, a respiratory device further comprises a respiratory gas supply. A respiratory gas inlet 120 is shown attached to the respiratory device, providing gas, such as pure oxygen or mixed oxygen to the passageway. An airflow resistor 24 is included within the passageway which may modify inspiratory and/or expiratory resistance during any or all portions of the respiratory cycle. In some versions of the device, the airflow resistor 24 during exhalation may feature a flap mechanism in which the flap partially or completely occludes respiratory gas inlet 120, thereby only providing release of gas when the subject is inhaling and the flow resistor 24 is therefore open to some degree. The device that provides the respiratory gas may be permanently or non-permanently fixed, attached, or otherwise coupled to the holdfast, rim, or airflow resistor via a press fit, adhesive, or in some other fashion. In some cases, the respiratory gas supply may be an off-the-shelf device that that provides respiratory gas, as is currently available from multiple manufacturers.

Figure 28:
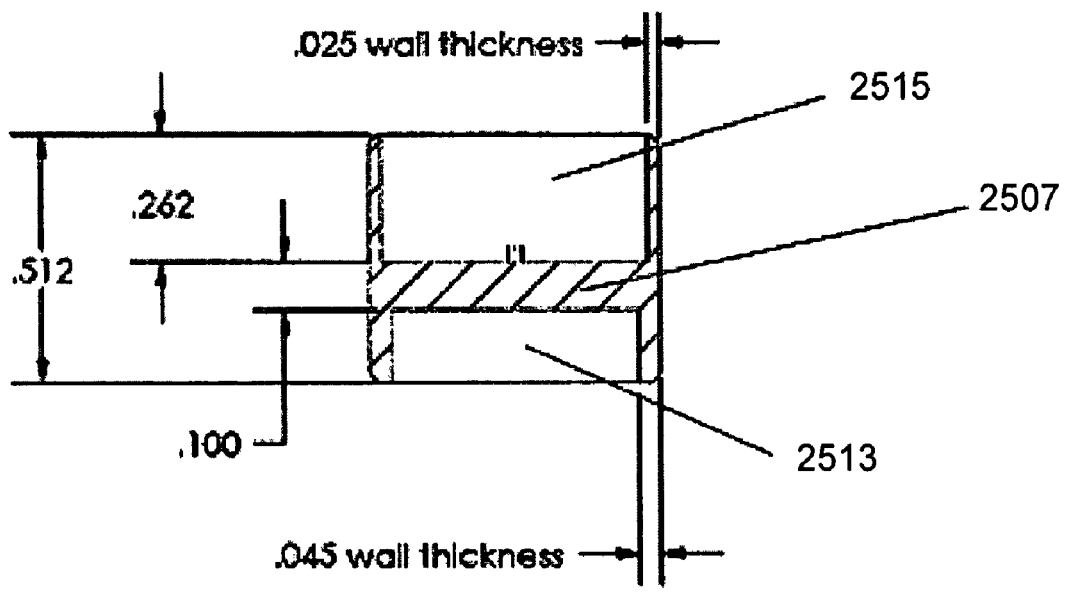

FIGS. 25 to 28 illustrate components of respiratory devices configured for use in a subject's nasal cavity, similar to the device illustrated in FIG. 29. FIG. 25 shows a perspective view of a rim portion of a respiratory device. The rim is configured as a tubular body 2501. FIG. 26 shows a side view of this tubular body 2501. The tubular body 2501 has openings at the distal and proximal ends to allow air to flow through the internal passageway formed by the rim. This passageway can be seen in FIG. 27, looking down through one end of the rim. In this variation, two flap valve supports 2507, 2507' are shown spanning the passageway. The flap valve is not shown. Two valve aligners 2511, 2511' project off of one of bars of one of the valve supports 2507'. In this variation, these valve aligners are posts which can pass through the flap valve (not shown) and orient and secure the flap. In FIGS. 27 and 28, measurements (given in inches) are shown merely to illustrate one example of dimension that may be used. Other variations may include other dimensions).

Figure 30B:
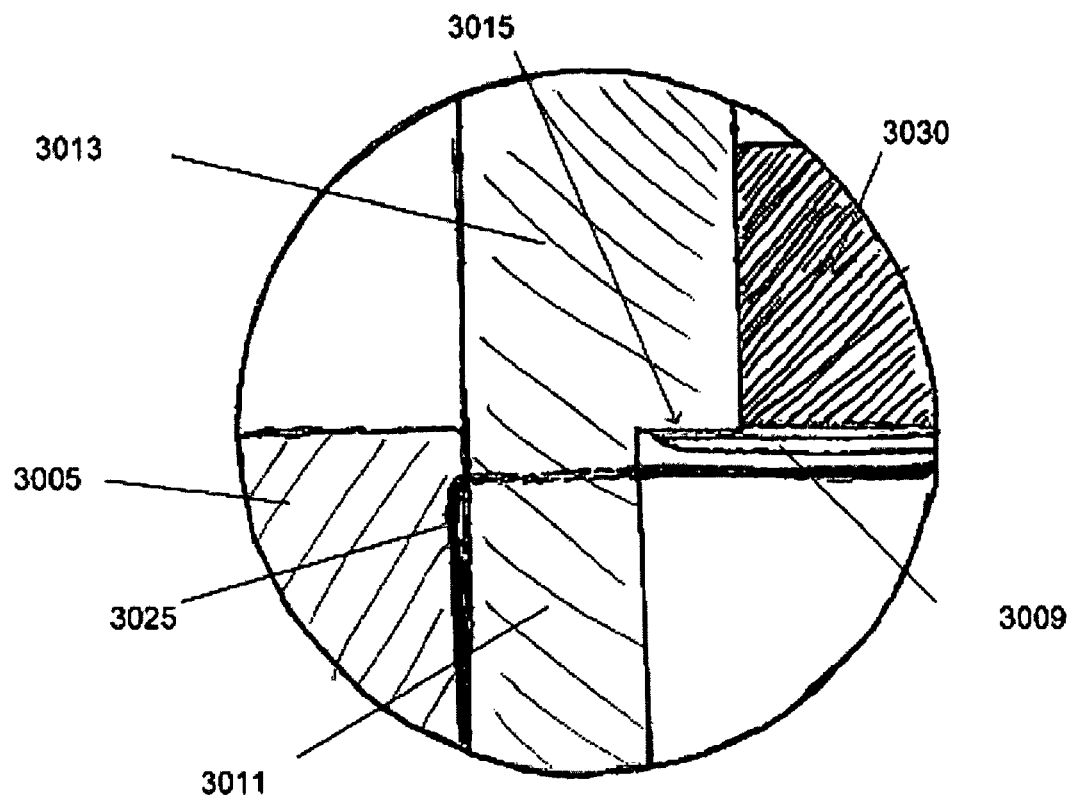

FIG. 28 shows a cut-away side view of half of this rim showing part of a valve support (crossbar 2507). As described above, the rim includes a proximal region 2513 and a distal region 2515. The distal region may be inserted into the subject's nasal cavity first, so that air leaving the subject's lungs during exhalation passes from the distal end towards the proximal end. The distal portion of the rim corresponds to the distal end of the device. As mentioned above, a flap valve (not shown) may contact the flap valve support 2507. In embodiments such as the one shown here, the device includes a distal region that is configured so that the flap valve cannot extend past the opening at the distal-most end of the device (e.g., the distal-most edge of the rim), even when the flap valve is completely opened. Thus, the rim may protect the flap valve and allow its full range of motion. Also as described above, the wall thickness of the distal region 2515 is thinner than the wall thickness of the proximal region 2513. This discrepancy in wall thickness may form a lip or ledge within the passageway at the interface between the proximal and distal region of the device. A lip is not visible in the device shown in FIG. 27 or 28 because it is blocked from view by the crossbar spanning the central portion of the passageway. FIGS. 30*a* and 30*b* illustrate another example of a respiratory device in which this lip (which forms a valve seal surface) is visible.

FIG. 29 shows a perspective view of a respiratory device incorporating the rim shown in FIGS. 25-28. This device includes a tubular body 3001, a passageway 3003, and a holdfast 3005 connected to the distal region of the tubular body. The holdfast shown is a foam ring that ensheathes the elliptical tubular body. A cross-sectional view of this device (taken through line A-A' along the midline of the flap valve) is shown in FIG. 30*a*, and FIG. 30*b* shows detail of the indicated region (B'). In FIGS. 30*a* and 30*b* the flap valve 3009 is shown in the closed position, and a valve seal surface is located between the flap valve 3009 by the lip 3015 formed on the inner wall of the tubular body 3001. The edge of the flap 3009 rests against this valve seal surface (lip 3015). In this variation, the lip 3015 is formed from the different wall thicknesses of the distal region 3011 and the proximal region 3013 of the rim. These regions have the same outer diameter (OD), but different inner diameters (IDs).

The flap valve shown in FIGS. 30*a* and 30*b* is aligned within the passageway of the device by valve aligners 3021, and the flap can be secured in position by including a flap valve lock around which the valve can move. In the variation shown in FIGS. 30*a* and 30*b*, the flap valve lock is configured as a fulcrum support 3025 and is formed from a flexible material such as a suture. In general, the flap valve lock secures the flap of the flap valve (in this example, the flexible flap) so that it cannot separate from the device. The flap valve lock in FIGS. 30*a* and 30*b* is connected to the valve aligners 3021. The flap valve lock (suture) passes through the wall of the passageway, over the flap valve, and through the posts of the valve aligner. Thus, the suture 'locks' the flap in place. A flap valve lock may prevent the flap valve from disengaging from the valve aligner. For example, a flap valve lock may comprise a cap or projection that communicates with the valve aligner to prevent the flap valve from disengaging from the valve aligners.

In some variations, the flap valve lock may also act as a fulcrum support. A fulcrum support is typically a point, line or surface about which the flap valve moves. Any appropriate fulcrum support may be used, including a pin (e.g., comprising a metal, plastic or other polymer, etc.), or fibrous material (e.g., thread, suture, etc.) that acts as a fulcrum, supporting the flap valve so that it can move. In some variations, a flap valve does not use a fulcrum support. As shown in FIG. 30*a*, the fulcrum support 3025 extends across the width of the flap valve, passing through the valve aligners 3021, and into the sides of the rim. As mentioned above, this suture is also a flap valve lock that secures the flap in place (shown in detail in FIG. 30*b*). In general, however, a fulcrum support does not have to be a flap valve lock. Likewise, a flap valve lock does not have to be a fulcrum support. For example, a flap valve lock may comprise a cage structure (e.g., a wire cage) that surrounds the flap valve, preventing it from leaving the device, but does not provide a point, line, or surface about which the valve moves. Thus, a respiratory device may include a flap valve lock but not a fulcrum support. A respiratory device may also include a fulcrum support but not a flap valve lock.

FIG. 31a shows a view looking into a respiratory device (similar to the one shown in FIG. 30) from the distal end. The flap valve 3009 is shown in outline only, so that two valve supports 3105, 3105' can be seen. A valve seal is not shown in FIG. 31a. The two valve supports form a cross-shape within the passageway of the device. When the flap valve is closed (as illustrated), the flap may rest against the valve supports. The flap valve also includes four leak paths 3109 through the flap valve through which air may pass. These leak paths are shown as small holes, though any appropriate shape (e.g., round, square, oval, polygonal, etc.) may be used. Two additional holes are shown through which valve aligners 3111 pass to align and/or secure the flap valve. These exemplary valve aligners comprise two posts projecting from the valve support.

As described above, the flap valve 3009 may be a thin and flexible piece of silicone. This flap may be any appropriate thickness that allow it to be flexible (e.g., to bend from the open and closed positions). For example, the flap may comprise silicone that is approximately 0.002 inches thick. In this example, the flap valve is matched to the cross-sectional shape of the passageway, so that it may close off passage through the passageway when in the closed position. The exemplary respiratory devices shown above may be manufactured by any appropriate method. For example, the tubular body, flap valve supports, and valve positioners may be injection molded as a single component from a material such as polyether block amide (e.g., PEBAX®), which is somewhat flexible and biocompatible. The flap valve may be die cut from a sheet of silicone (e.g., medical grade silicone), including any leak paths. These components may be manually or automatically assembled, and the flap valve may be secured in place by a fulcrum support (e.g., a suture, as described above), an adhesive, or the like. A holdfast may be attached to the outer portion of the tubular body, particularly the distal region of the tubular body.

As mentioned, the holdfast may be polyurethane foam. The foam may be pre-molded into the appropriate shape, or it may be cut (e.g., die cut, water jet cut, laser cut, etc.) into a ring or other appropriate shape and attached to the tubular body. For example, the foam may be attached via an adhesive (e.g., tape, glue, etc.). In one variation, the foam is cut from a strip of foam that is attached around the tubular body. The foam may be any appropriate size so that the device is secured within a subject's nasal cavity. In some variations, the foam is between about ¼ and ⅛ of an inch thick. The thickness of the foam holdfast may vary around the diameter of the device. For example, the foam holdfast may be thicker at the ends of an elliptical cross-section so that it conforms better to the shape of a subject's nasal cavity, particularly in the region immediately within the subject's nose, past the nares.

The aforementioned devices and methods of using them may provide a first airflow resistance to airflow from proximal airways to distal airways (inhalation) and a second flow resistance to airflow from distal airways to proximal airways (expiration). In some of the respiratory devices described herein, the resistance to expiration is sufficient to cause the subject to inhale prior to reaching a complete expiration, causing PEEP during the expiration cycle. In some respiratory devices described herein, when expiratory airflow and/or expiratory airway pressures fall below a threshold (one that is too low to keep an airflow resistor mechanism open), expiration airflow will be stopped, leading to PEEP. As a result, normal inspiration, normal expiration, and PEEP are accommodated while offering potential benefits to the subject, including clinical benefits.

Figure 33:
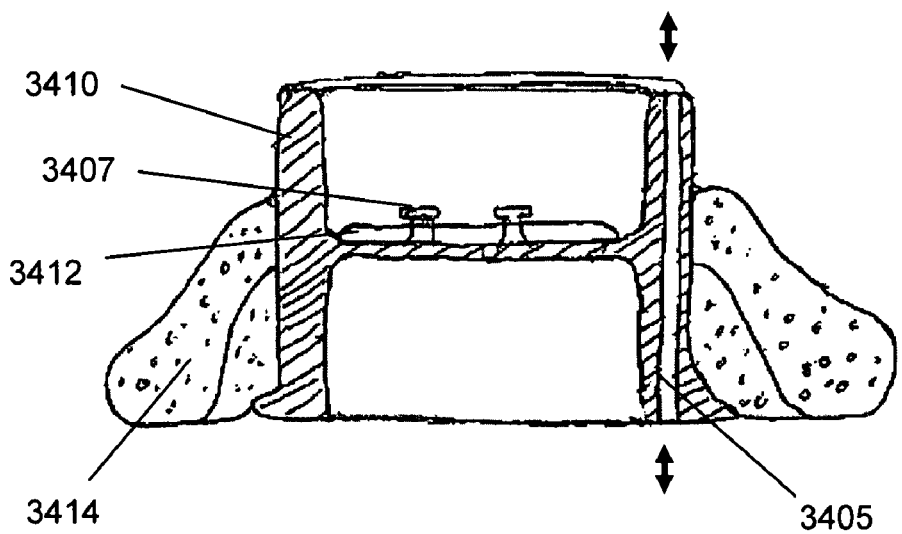
FIG. 33 is a cross-sectional view of one variation of a nasal respiratory device.

FIG. 33 is a cross-sectional view though one variations of a nasal respiratory device having a flap valve, similar to the view shown in FIG. 30a. In this example, a leak pathway through a non-flap portion of the device 3405. The flap 3412 is attached to the rim (or body) 3410 of the device by two posts 3407, and each post has a flap lock 3408, which is a cap-like stop on the end of the posts in this variation. These posts 3407 act as flap valve aligners. The body 3410 is surrounded by a tapered, foamed holdfast 3414 that may be used to secure the device at least partially within a subject's nostril. The flexible flap may bend to open during inhalation (while staying secured by the flap valve aligners 3407) but is prevented from opening during exhalation because of a flap valve support (not apparent in this section). Air may pass through the leak path through the body of the device 3405 either when the flap is closed, or when it is open, as indicated by the double arrows. In addition, leak paths on the flap 3403 are visible in the top view of FIG. 34.

Figure 34:
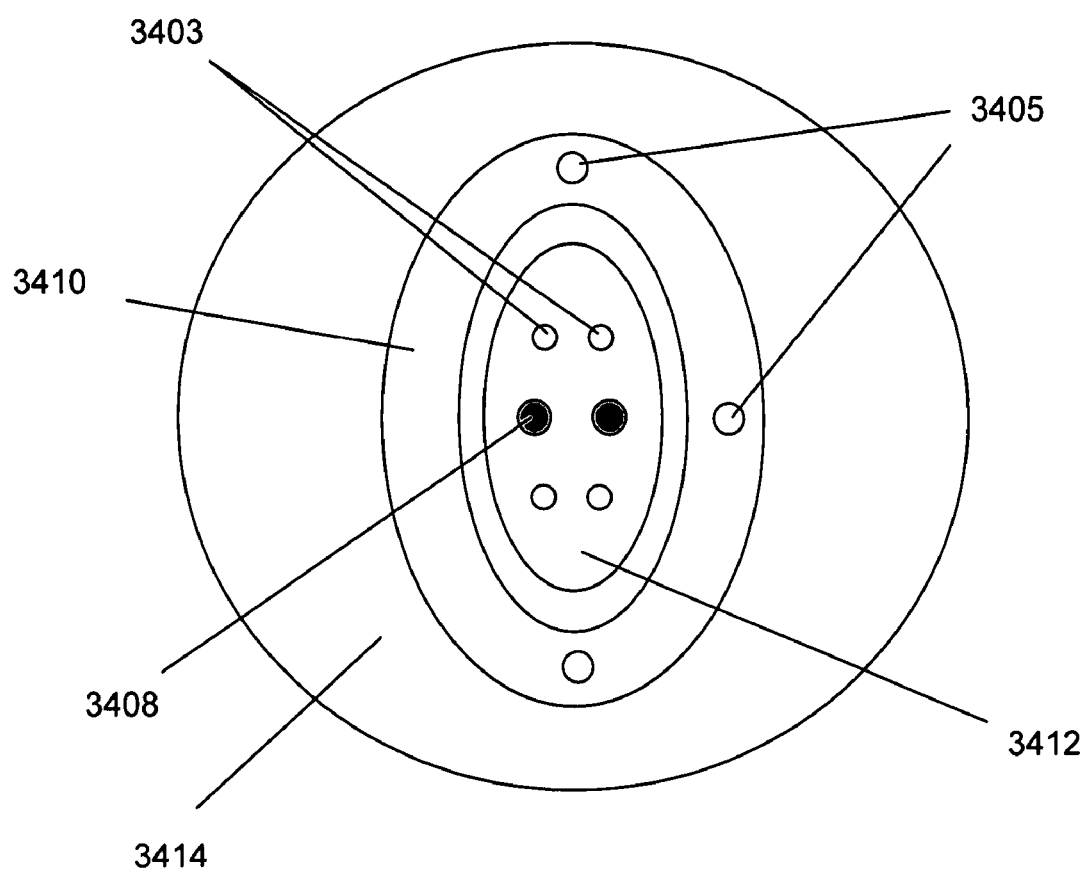
FIG. 34 is a top view of the same device shown in FIG. 33.

FIG. 34 is a top view of the same valve shown in FIG. 33. In FIG. 34, the rim body is an oval shape, as described above, and the foam holdfast 3414 is substantially circular. The flap 3012 includes leak paths 3403 in addition to the leak paths through the rim 3405. Three non-flap leak paths are shown.

Uses of the Respiratory Devices

The respiratory devices and methods described herein may be used for a variety of therapeutic and non-therapeutic purposes. A description of some of these uses is given below. The respiratory devices and methods described herein may be used in other ways as well, and these examples are not to be considered exhaustive.

Generally, the respiratory devices described herein may improve the respiratory and cardiovascular function of a person in need thereof (e.g., a patient or subject). Thus, these respiratory devices may be used therapeutically, for example, to cure, treat or ameliorate the symptoms of a variety of medical disease states. Furthermore, the respiratory devices may be useful in generally improving the health and well being of any person.

Disease states which may be treated by the devices and methods described herein include but are not limited to: heart failure (right-sided and/or left-sided), COPD, pulmonary edema, sleep apnea (including obstructive and/or central), sleep-disordered breathing, Cheyne-Stokes respiration, insomnia, snoring and other sleep disorders, asthma, bronchomalacia, acute lung injury, ARDS, sinusitis, allergies, hey fever, nasal congestion, cystic fibrosis, hypoxemic respiratory failure, gastroesophageal reflux disease, hiatal hernia, heartburn, hypertension, myocardial infarction, arrhythmia, cardiomyopathy, cardiac valve disease (either stenosis or regurgitation of the mitral, aortic, tricuspid, or pulmonic valves), stroke, transient ischemic attack, increased cerebral pressure, a variety of inflammatory diseases, and degenerative neurologic conditions. Moreover, the devices may be beneficial for subjects being weaned off mechanical ventilation, as well as post-operative patients.

The increased pressure within the airways may reduce the amount and frequency of pulmonary edema, a common consequence of heart failure. Afterload and preload on the heart may also be affected; for example, afterload and preload may be decreased in subjects with heart failure. Filling pressures may be increased or, more likely, decreased. Decreasing filling pressure may potentially benefit subjects with failing hearts. Gas exchange may improve in many cases, leading to increases in $po_2$ and decreases in $pCO_2$. In some cases, the level of $pCO_2$ may actually increase or become more stable and less likely to fluctuate. This increase in the stability of $pCO_2$ levels may lead to profound benefits in subjects with central sleep apnea and in subjects with Cheyne-Stokes breathing, for example. Oxygen saturation levels may improve. Oxygen desaturations which may result from apneas or hypopneas may no longer drop as far. For example there may be fewer oxygen desaturations to the 80-89% range. Fewer oxygen desaturations may drop below 90%. Duration of desturations may also be reduced. The use of the device to reduce oxygen desaturations (perhaps leading to performance enhancement) while awake or asleep may represent a viable market opportunity for the device.

In some cases, the use of an expiratory resistor will interfere with loop gain, and will thus promote more stable breathing. In other cases, the device will reduce the amplitude, duration, and frequency of snoring.

Any location within the body that is exposed to respiratory airflow (including but not limited to the upper airway, trachea, bronchi, nasopharynx, oropharynx, nasal cavity, oral cavity, vocal cords, larynx, tonsils and related structures, back of the tongue, sinuses, and turbinates) may benefit from the increased airway pressure and increased duration of expiratory airflow . In some cases, there will be a reduction in swelling and edema in these locations, leading to increased diameters of the airways and conduits in which the airflow passes. This leads to less of a tendency for these structures to collapse upon inhalation. Moreover, these structures may be less prone to create noise on inspiration or expiration, thereby reducing the quantity and/or quality of snoring. Put another way, the reduction of edema in the airways may make it less likely that these structures will collapse and may reduce the volume and frequency of snoring, apnea, or hypopnea. Furthermore, reduction in swelling and edema and improved lymphatic flow due to these positive pressures may reduce nasal congestion, inflammation, and sinusitis for example.

The respiratory device may also increase lung compliance. For example, lung compliance may increase partially if fluid which might otherwise be in the lung and alveoli is driven away by the increased airway pressure. This increased lung compliance may make it easier to breathe and may require less effort and force on the part of the subject to displace the diaphragm a certain distance to achieve a certain tidal volume. Moreover, increased lung compliance may decrease the pressure differential between the alveoli and mouth. As this pressure differential decreases, it becomes less likely that an inhalation attempt will induce a collapse of the upper airway. Thus, an increase in lung compliance may herald a reduction in the frequency or severity of obstructive sleep apnea or hypopnea episodes. Similarly, snoring frequency and severity (volume) may be reduced for similar reasons.

The respiratory device may also improve ejection fraction. This effect may be mediated via increases in intra-thoracic pressure and alterations in transmural pressures and the beneficial effects on preload and afterload on the failing heart. In addition to left-sided benefits to the heart, there may also be benefits afforded to the right side of the heart. Improving ejection fraction with the respiratory devices described herein may result in positive short- and long-term changes to the energetics and biologic properties of the heart tissue. Some of these positive changes may mimic the positive remodeling changes seen in hearts treated with various complicated cardiac support devices such as those developed by Acorn Cardiovascular (St. Paul, Minn.) and Paracor Medical (Sunnyvale, Calif.). These expiratory resistors use the subject's own intra-thoracic pressure to "support" the subject's heart. Moreover, because the support potentially provided by the respiratory devices described herein is not limited to just the ventricle, it may support the atria, which can also be severely affected by heart failure and other cardiac or pulmonary diseases. There may be reductions in left ventricular and left atrial sizes, both in the shorter and longer term. Furthermore, cardiac sympathetic activation may be reduced, and cardiac output may be increased or decreased depending on the nature of the resistance provided.

There are a variety of other beneficial effects of enhanced expiratory resistance and increases in intra-thoracic pressure that may be achieved with the respiratory devices described herein. Examples include decreased heart rate and blood pressure. There may be a reduction in the number of arrhythmias, including but not limited to atrial/supraventricular and ventricular fibrillation, atrial/supraventricular and ventricular tachycardias, heart block, and other common arrhythmias. Thus, the respiratory devices described herein may also reduce the incidence of sudden cardiac death and other cardiac disorders. Furthermore, coronary perfusion may be expected to increase. Further, expiratory resistance and increased intra-thoracic pressures may lead to improvements in gastroesophageal reflux disease (i.e., heartburn), gastritis, Barrett's esophagus, esophageal cancer, hiatal hernia, and other causes of diaphragmatic hernia. This effect may be mediated by the compression of the esophagus located within the thorax due to the increased intra-thoracic pressures. As a result, food and other stomach contents may no longer be able to reflux superiorly into the esophagus, which is otherwise common when subjects are lying down. Furthermore, hernias (primarily hiatal) may be reduced and pushed back into the abdomen by the increased intra-thoracic pressure. The use of these respiratory devices may have beneficial effects on other gastroenterologic conditions beyond those already described.

Cardiac valve disease, including but not limited to mitral, tricuspid, pulmonic and aortic regurgitation, and mitral, tricuspid, pulmonic and aortic stenosis may also benefit from the respiratory devices described herein. In particular, the respiratory device may effect mitral regurgitation and may help prevent further annular dilatation (a byproduct of heart failure and generalized heart dilation).

Use of the respiratory devices described herein will result in a reduction in respiratory rate, which may be very helpful in diseases such as COPD, asthma, hyperventilation, and anxiety disorders including panic attacks, among others. The ratio of inspiratory time to expiratory time (I:E ratio) may be decreased with the device. Tidal volumes may increase as well. For example, in COPD, the increased resistance may facilitate improved expiratory function. This may also allow the subject to benefit from larger tidal volumes and increased minute ventilation. In embodiments in which the respiratory device creates PEEP (positive end expiratory pressure), the amount of PEEP (or resistance generated by the device) may overcome some, or all, of the intrinsic PEEP that is common in subjects with COPD. In subjects with COPD or other pulmonary disorders, gas exchange may improve. In this case, gas exchange refers to the removal of $CO_2$ from the body and addition of $O_2$ into the blood stream from inspired air. Thus, $po_2$ may increase and $pCO_2$ may decrease, particularly in subjects with COPD, but more generally in all subjects treated with the device. Moreover, oxygen saturation may increase, reflecting an increase of oxygen binding to hemoglobin.

Other benefits offered by the respiratory device may include a reduction in diaphragm fatigue and improved efficiency of the accessory muscles of inspiration. This may make breathing significantly easier in subjects with pulmonary disease, and more specifically COPD and cystic fibrosis.

As previously mentioned, the respiratory devices described herein may decrease respiratory rate. It has been shown that slowed breathing techniques can lead to a reduction in blood pressure. Thus, the device may reduce blood pressure in a subject, including subjects with hypertension (systemic and pulmonary). The reduction in blood pressure may be systolic and/or diastolic. Reductions in blood pressure may be on the order of 1-70 mm Hg systolic or diastolic. This may bring the subject to normal (<140/80 mm Hg) or near normal (<160/100 mm Hg) levels. In subjects who are being treated for hypertension, the device could be used as an adjunctive therapy to drugs or as a stand-alone therapy in some subjects. In some versions, a respiratory device as described herein may be used for short periods (minutes, hours, or longer) over a span of days to weeks to months to offer longer term benefits for weeks or months after the cessation of therapy. Treatments may last 15 seconds to 24 hours and may be repeated over a regular or irregular interval, for example, on the order of hours to days. The devices may be worn at night or day, while awake or during sleep, to slow respiratory rate. A reduction in blood pressure and/or heart rate may be seen while the device is in place, or after the device has been removed. This may be due to hormonal influences whose effects last longer than the period in which the device is in place. More specifically, the device may work though either a sympathetic or parasympathetic pathway.

Expiratory resistance may also prolong expiratory time, which may reduce the respiratory rate. Thus, the devices described herein may be used to reduce respiratory rate. This may have benefits in treating insomnia, since it may promote a sense of relaxation in the user, through increased parasympathetic stimulation, decreased sympathetic simulation, and/or other hormonal and non-hormonal effects. This may also promote a sense of well being or relaxation that may allow the user to fall asleep easier and quicker and improve sleep quality and quantity. Thus, the respiratory devices described herein represent a novel non-pharmacologic method of treating insomnia and promoting relaxation. The device may be used throughout the day and/or night to promote said relaxation and well being.

The respiratory devices described herein may also be used to treat or ameliorate disorders characterized by ineffective, non-productive, or otherwise disturbed inspiration (including but not limited to obstructive sleep apnea or restrictive pulmonary disease). For example, with the device in place, a subject may be more likely to have slightly elevated lung volumes after exhalation. Put another way, more air than normal may be present in the lungs after exhalation when using some versions of the device. Fewer alveoli may be collapsed; thus inhalation may be easier because it will require less effort to re-open the alveoli during the subsequent breath. Moreover, pulmonary congestion and pulmonary edema may also be reduced, so compliance may be improved. As a result, it may require less effort for subjects to inhale. It follows that a smaller pressure differential (between the alveoli and the mouth) will be required. The smaller the pressure differential, the less likely that the subject's conducting airways (including the upper airways and pharyngeal tissues) will collapse, thus reducing the likelihood of obstructive sleep apnea, hypopnea, and snoring.

Infectious diseases may also benefit from the respiratory devices described herein. These diseases include but are not limited to pneumonia (community and hospital acquired), tuberculosis, bronchitis, HIV, and SARS.

The respiratory devices may also be useful in pulmonary or cardiac rehabilitation. For example, the device may find use in subjects with chronic pulmonary disease including but not limited to chronic bronchitis, emphysema, asthma, pulmonary fibrosis, cystic fibrosis, and pulmonary hypertension. Alternatively, the devices may benefit subjects with cardiac disease, including but not limited to: angina, myocardial infarction, right or left sided heart failure, cardiomyopathy, hypertension, valve disease, pulmonary embolus, and arrhythmia.

Subjects with obesity may also benefit from the use of the respiratory devices described herein. Obesity can contribute to exercise intolerance partially because it increases the metabolic requirement during activity and alters ventilatory mechanics by reducing functional residual capacity (FRC) and promoting atelectasis. Obesity may also reduce cardiac reserve, since a higher than normal cardiac output response is required during physical activity. This in turn may cause systemic hypertension, which increases left ventricular afterload. Thus, the device, through its potential reduction in atelectasis and beneficial effects on FRC, cardiac output, and blood pressure may be useful in subjects with obesity.

It has been suggested that expiratory positive airway pressure (as induced by the subject devices) may increase neural drive to the muscles that serve to maintain upper airway patency. Furthermore, FRC increases may improve length-tension relationships of the inspiratory muscles, allowing inspiratory pressures to decrease. This reduction of inspiratory pressure would thus make it less likely for the upper airway to obstruct, presumably due to a reduction in the transmural pressure gradient. As previously suggested, expiratory positive airway pressure may improve ventilation-perfusion relationships which may improve oxygen saturation.

Furthermore, it is known that the upper airway partially or completely occludes during the expiratory phase of the breaths preceding an occlusive apnea. It is this narrowing of the upper airway at end-expiration that sets the stage for total occlusion during the next inspiration as subatmospheric pressures are generated within the airway. Expiratory positive airway pressure may therefore prevent airway narrowing during expiration, thus reducing the propensity toward total occlusion during inspiration. The phenomena of lung hysteresis may also provide therapeutic benefit.

The subject devices are also expected to improve sleep quality, duration and architecture.

The respiratory devices may also be used by athletes, for example, during both aerobic and non-aerobic activities, partially because of the potentially beneficial direct effects on the heart and on gas exchange. In some versions, the respiratory device may be oversized, to increase the amount of inspiratory airflow, potentially increasing the amount of oxygen transmitted to the lungs for gas exchange.

The respiratory devices described herein may also be used for therapeutic and non-therapeutic effects on sleep. Sleep quality may be improved, with more slow-wave sleep, fewer arousals, and improved REM sleep. The user may have more productive sleep and may be less tired during the day. Furthermore, the beneficial effects of the device may extend beyond the period of use, and into the daytime as well, even when the device's use is limited to the night (e.g., when the user is sleeping). In some cases, sympathetic discharge may be reduced and/or parasympathetic discharge may be increased. Thus, the device may have positive benefits on the autonomic nervous system. This may offer beneficial systemic effects as well as local effects, some of which have already been described.

The respiratory devices described herein may also be used in other locations besides the nasal and oral cavities. Indeed, any location in the body that serves as an entry or exit location for respiratory airflow or serves as a conducting airway or conduit for airflow may benefit from the use of the devices described herein. For example, a device may be used within, on the external surface of, or near a stoma site (e.g., for use in a subject after a tracheostomy).

Inflammation (which is present in a variety of disease states) may also be reduced using the respiratory device, possibly via the aforementioned parasympathetic or sympathetic mediated effects and/or effects of the vagus nerve and its stimulation. The treatment of any condition mediated by an inflammatory cytokine cascade is within the scope of the devices and methods described herein. In some embodiments, the respiratory device is used to treat a condition where the inflammatory cytokine cascade is affected through release of pro-inflammatory cytokines from a macrophage. The condition may be one where the inflammatory cytokine cascade causes a systemic reaction, such as with septic shock. Alternatively, the condition may be mediated by a localized inflammatory cytokine cascade, as in rheumatoid arthritis. Examples of conditions which may be usefully treated using the respiratory devices described herein include, but are not limited to: appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, diabetes, ankylosing spondylitis, Berger's disease, Retier's syndrome, or Hodgkins disease.

Furthermore, the respiratory devices and methods of using them may be used by or applied to a variety of different types of animals. Representative animals with which the methods and devices find use include, but are not limited to: canines; felines; equines; bovines; ovines; etc. and primates, particularly humans. The respiratory devices described herein may also be packaged for use. For example, the respiratory devices may be packaged individually or as a set (e.g., in sets of pairs, particularly in variations in which an individual device is used with each nostril). Furthermore, the packaging may be sterile, sterilizable, or clean.

The respiratory devices described herein may also be provided as part of a kit that includes at least one of the devices. Examples of kits may include a respiratory device and instructions for how to use the device. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. The instructions may take any form, including complete instructions on how to use the device, or references, directing a user to using additional sources for instructions (e.g., a website address with which instructions posted on the world wide web).

The device may be used in a clinical study, wherein said clinical study involves comparing sleep data from a subject with the device in place to sleep data from the same subject without the device in place. Any duration of the sleep study shall suffice, from minutes to hours.

The device may be used in subjects who have already undergone ENT surgery to help their sleep apnea and/or snoring. This combination of surgery and use of the device may thus reduce AHI, snoring and other relevant parameters. Similarly, the use of weight reduction or sleep position therapy may find use in conjunction this device.

As mentioned above, a respiratory device adapted for use in the nasal cavity may be placed into one or both of a subject's nostrils by medical personnel or by the subject himself. The respiratory device may be secured in place in the subject's nostrils by the interaction between the nostril cavity and the holdfast of the device. The device may be worn during the night or day, while the subject is awake or sleeping. In some cases, the device may be worn around the clock. For example, the device may be worn at night to prevent snoring.

All publications and patent applications cited in this specification are herein incorporated by reference in their entirety, as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nasal respiratory device configured to be worn while sleeping and to be secured in communication with a subject's nasal cavity, the device comprising:
    an airflow resistor configured to inhibit expiration more than inhalation; and
    a holdfast configured to secure the device in communication with the subject's nasal cavity;
    wherein the nasal respiratory device has a resistance to expiration that is between about 0.001 and about 0.25 cm $H_2O$/(ml/sec), and a resistance to inhalation that is between about 0.0001 and about 0.02 cm $H_2O$/(ml/sec), when resistance is measured at 100 ml/sec.

2. The nasal respiratory device of claim 1, wherein the nasal respiratory device has a resistance to expiration that is between about 0.03 cm $H_2O$/(ml/sec) and about 0.2 cm $H_2O$/(ml/sec) when resistance is measured at 100 ml/sec.

3. The nasal respiratory device of claim 1, wherein the nasal respiratory device has a resistance to expiration that is between about 0.03 and about 0.15 cm $H_2O$/(ml/sec) when resistance is measured at 100 ml/sec.

4. The nasal respiratory device of claim 1, wherein the nasal respiratory device has a resistance to inhalation that is between about 0.001 and about 0.02 cm $H_2O$/(ml/sec) when resistance is measured at 100 ml/sec.

5. The nasal respiratory device of claim 1, wherein the nasal respiratory device has a resistance to inhalation that is between about 0.001 and about 0.01 cm $H_2O$/(ml/sec) when resistance is measured at 100 ml/sec.

6. The nasal respiratory device of claim 1, wherein the airflow resistor comprises a flap valve.

7. The nasal respiratory device of claim 1, further comprising at least one leak path.

8. The nasal respiratory device of claim 7, wherein the at least one leak path is not formed though a movable portion of the airflow resistor.

9. The nasal respiratory device of claim 1, further comprising a nasal airflow monitor configured to be positioned within or near the nasal respiratory device.

10. The nasal respiratory device of claim 9, wherein the nasal airflow monitor is selected from the group consisting of: a nasal cannula and a thermistor.

11. A method of treating a disorder in a sleeping subject, the method comprising:
   allowing the subject to breathe through the mouth without additional resistance while inhibiting nasal expiration more than nasal inhalation while sleeping; and
   inhibiting nasal expiration more than nasal inhalation by providing a resistance to nasal expiration that is between about 0.001 and about 0.25 cm $H_2O$(ml/sec), and a resistance to nasal inhalation that is between about 0.0001 and about 0.02 cm $H_2O$/(ml/sec), measured at a flow rate of 100 ml/sec.

12. The method of claim 11, further comprising securing a respiratory device in communication with the subject's nasal cavity, wherein the respiratory device comprises an airflow resistor that inhibits expiration more than inhalation.

13. The method of claim 11, wherein the disorder treated is selected from the group consisting of: sleep disordered breathing or snoring.

14. A method of treating a disorder in a sleeping subject, the method comprising:
   securing a nasal respiratory device in communication with a subject's nasal cavity, wherein the respiratory device comprises a flap valve and a flap valve support adjacent to the flap valve, wherein the flap valve support is configured to prevent the flap valve from opening in more than one direction; and
   inhibiting nasal expiration more than nasal inhalation in the sleeping subject by providing a resistance to nasal expiration that is between about 0.001 and about 0.25 cm $H_2O$/(ml/sec), and a resistance to nasal inhalation that is between about 0.0001 and about 0.02 cm $H_2O$/(ml/sec), measured at a flow rate of 100 ml/sec.

15. The method of claim 14, wherein the disorder treated is selected from the group consisting of: sleep disordered breathing or snoring.

16. A method of treating a disorder in a sleeping subject, the method comprising:
   securing a nasal respiratory device in communication with a subject's nasal cavity, wherein the respiratory device comprises an airflow resistor configured to inhibit nasal expiration more than nasal inhalation; and
   inhibiting nasal expiration more than nasal inhalation in the sleeping subject by providing a resistance to nasal expiration that is between about 0.001 and about 0.25 cm $H_2O$/(ml/sec), and a resistance to nasal inhalation that is between about 0.0001 and about 0.02 cm $H_2O$/(ml/sec), measured at a flow rate of 100 ml/sec.

17. The method of claim 16, wherein the disorder treated is selected from the group consisting of: sleep disordered breathing or snoring.

18. A method of increasing a subject's tolerance of a nasal device when treating a sleep disorder by reducing the sensation of expiratory resistance when awake, the method comprising:
   placing a nasal respiratory device in communication with a subject's nasal cavity but not covering the subject's mouth, wherein the nasal respiratory device includes an airflow resistor configured to inhibit expiration more than inspiration;
   securing the nasal respiratory device in communication with the subject's nasal cavity; and
   instructing the subject to breathe through the mouth when awake or falling asleep.

19. The method of claim 18 wherein the step of instructing the subject to breathe through the mouth when awake or falling asleep comprises instructing the subject to breathe out through the mouth when awake or falling asleep.

20. The method of claim 18 wherein the step of instructing the subject to breathe through the mouth when awake or falling asleep comprises instructing the subject to breathe in and out through the mouth when awake or falling asleep.

21. A method of monitoring treatment of a sleep disorder comprising:
   securing a nasal respiratory device in communication with the subject's nasal cavity, wherein the respiratory device includes an airflow resistor configured to inhibit expiration more than inspiration;
   attaching a nasal airflow monitor to the nasal respiratory device or the patient's face; and
   monitoring nasal airflow.

22. The method of claim 21, wherein the step of attaching a nasal airflow monitor comprises attaching a nasal cannula to the nasal respiratory device.

23. The method of claim 21, wherein the step of attaching a nasal airflow monitor comprises attaching a thermistor to the nasal respiratory device.

24. A nasal respiratory device configured to be secured in communication with a subject's nasal cavity to treat a sleeping disorder, the device comprising:
   an airflow resistor configured to inhibit expiration more than inhalation;
   a holdfast configured to secure the device in communication with the subject's nasal cavity but not covering the subject's mouth; and
   a connector for a nasal airflow monitor configured to connect a nasal airflow monitor to the nasal respiratory device and monitor the subject's respiration.

25. The nasal respiratory device of claim 24, wherein the nasal airflow monitor is selected from the group consisting of: a nasal cannula and a thermistor.

26. A method of increasing a subject's tolerance of a nasal device when treating a sleep disorder by reducing the sensation of expiratory resistance when awake, the method comprising:
   placing a nasal respiratory device in communication with a nasal cavity but not covering the mouth, wherein the nasal respiratory device includes an airflow resistor configured to inhibit expiration more than inspiration;
   securing the nasal respiratory device in communication with the nasal cavity;
   breathing through the mouth when awake or falling asleep; and
   breathing through the nose when asleep.

* * * * *